(12) United States Patent
Sayers, III et al.

(10) Patent No.: US 8,756,124 B1
(45) Date of Patent: *Jun. 17, 2014

(54) SYSTEMS AND METHODS FOR TRACKING AND TRACING PRODUCTS THROUGH A SUPPLY CHAIN UTILIZING UNIQUE URLS

(71) Applicants: Foster Joseph Sayers, III, Providence, RI (US); Albert Ho, Boston, MA (US); Charles Hyung Kim, Boston, MA (US)

(72) Inventors: Foster Joseph Sayers, III, Providence, RI (US); Albert Ho, Boston, MA (US); Charles Hyung Kim, Boston, MA (US)

(73) Assignee: AgileQR, Inc., Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/925,039

(22) Filed: Jun. 24, 2013

Related U.S. Application Data

(63) Continuation of application No. 13/766,738, filed on Feb. 13, 2013, now Pat. No. 8,533,075.

(51) Int. Cl.
G06Q 10/00 (2012.01)
G06Q 99/00 (2006.01)
G06F 17/00 (2006.01)

(52) U.S. Cl.
USPC ............. 705/28; 705/303; 705/317; 705/318; 235/375

(58) Field of Classification Search
None
See application file for complete search history.

(56) References Cited

U.S. PATENT DOCUMENTS

| 6,943,736 | B2* | 9/2005 | Noro et al. | 343/700 MS |
| 7,419,097 | B2* | 9/2008 | Lee et al. | 235/462.11 |
| 8,261,972 | B2* | 9/2012 | Ziegler | 235/375 |
| 2007/0215685 | A1* | 9/2007 | Self et al. | 235/375 |
| 2011/0289010 | A1* | 11/2011 | Rankin et al. | 705/313 |
| 2013/0036061 | A1* | 2/2013 | Alexander et al. | 705/303 |

* cited by examiner

Primary Examiner — Ryan Zeender
Assistant Examiner — Allen Chein
(74) Attorney, Agent, or Firm — American Patent Agency PC; Daniar Hussain; Karl Dresdner

(57) ABSTRACT

Embodiments of the present invention may be used in various regulation-heavy industries, such as pharmaceutical, biomedical, construction, energy, heavy industry, and similar industries with large regulatory and/or safety considerations. The present invention describes a track-and-trace solution based on unique item-level QR codes printed on product packaging and encoding unique URLs to enable granular, item-level product management. In some embodiments of the invention, the information presented to users who access these unique URLs is tailored based on product usability information provided from authorized supply chain participants, the role of the user in the supply chain, and/or regulation required data comprising product safety data as required by regulations from a regulatory agency. Embodiments of the invention may be used for the purposes of item authentication, anti-counterfeiting measures, product recall management, and the efficient distribution of supplementary product information.

20 Claims, 11 Drawing Sheets

SYSTEMS AND METHODS FOR TRACKING AND TRACING PRODUCTS THROUGH A SUPPLY CHAIN UTILIZING UNIQUE URLS

REFERENCE TO RELATED APPLICATIONS

The present application claims priority from U.S. Ser. No. 13/766,738, entitled "Systems and methods for biomedical track and trace," filed on Feb. 13, 2013, and issued on Sep. 10, 2013 as U.S. Pat. No. 8,533,075, which is hereby incorporated by reference in its entirety herein.

FIELD OF THE INVENTION

The present invention broadly relates to a system and method for biomedical product track and trace that simultaneously solves the problems of counterfeiting and inefficient recalls using codes deployed on product packaging.

BACKGROUND OF THE INVENTION

All pharmaceuticals and medical devices sold in the United States are subject to FDA regulations. Smart packaging as a track and trace technology platform for the biomedical industry that simultaneously solves the critical problems of counterfeiting and inefficient recalls is needed in the industry. The annual global market for pharmaceuticals in 2006 was $500 billion. In 2006, $40 billion was lost to counterfeit products globally, and that number was projected to reach $75 billion by 2010. Bio-pharma paperboard packaging is projected to grow 5% year-over-year and to reach $730 million by 2015. A recall of products in 2010 cost Johnson & Johnson $600 million. In September and October of 2012, 404 people were infected and twenty-nine people died from a meningitis outbreak that led to a total recall of all Ameridose products. The liabilities and expense from this recall are not yet known. It is known that as a result, Ameridose has notified 790 employees of pending layoffs, including 140 employees of an affiliated marketing company. Track and trace technologies have potential to reduce losses due to counterfeit products, manage recalls more efficiently in an effort to protect consumers and to reduce negative economic impacts, comply with FDA regulations, and provide relevant information to consumers in real time. Beyond drugs and medical devices, track and trace can be extended to food and other FDA-regulated products, as well as consumer electronics and practically anything that can be sold in a deceptive or broken state.

The FDA Amendments Act of 2007 promised track and trace guidelines but failed to deliver them. In the absence of guidelines there is inertia among bio-pharma companies and other organizations to adopt track and trace technology. Therefore, they need a technology that is future-proof, one that can be readily changed to meet the requirements of new regulations.

Therefore, it would be an advancement in the state of the art to provide a track and trace application for biomedical products that addressed the pressing needs of industry and the FDA. It is against this background that the various embodiments of the present invention were developed.

BRIEF SUMMARY OF THE INVENTION

Accordingly, one embodiment of the present invention is a collaborative method for tracking and tracing a biomedical product utilizing data received from numerous supply-chain participants, comprising the steps of printing, on a product packaging utilizing a printer, regulation required data about an individual item of a biomedical product contained within said product packaging from a manufacturer, then printing, on said product packaging utilizing the printer, a unique Quick Response (QR) code which encodes a unique Uniform Resource Locator (URL) having a one-to-one mapping with said individual item of said biomedical product, which when invoked, responds with a unique landing page showing at least said regulation required data, then receiving, via the unique URL, supply chain participant data about said individual item and a directive related to said supply chain participant data from an authorized supply chain participant, then initializing, utilizing a computer processor, a regulation rule based on the regulation required data that governs in part how said unique landing page is presented to different users over time, then initializing, utilizing the computer processor, a supply chain participant rule based on said supply chain participant data and said directive that governs in part how said unique landing page is presented to different users over time, then initializing, utilizing the computer processor, a user role rule based on a user role that governs in part how said unique landing page is presented to different users over time, then receiving, via the unique URL, a scan of said unique QR code by a scanning supply chain participant, then identifying, utilizing the computer processor, said scanning supply chain participant with said user role, and then applying, utilizing the computer processor, said regulation rule, said supply chain participant rule, and said user role rule to present said unique landing page to said scanning supply chain participant, wherein the unique landing page is customized based at least on supply chain participant data received from one or more other supply chain participants via the unique URL.

Another embodiment of the present invention is the collaborative method for tracking and tracing a biomedical product as described above, further comprising the steps of providing a printed Instructions for Use (IFU) document stored with said individual item of said biomedical product, said IFU document comprising printed instructions and the unique Quick Response (QR) code, then providing a most recent electronic version of said IFU document, wherein said unique landing page is configured to redirect to said most recent electronic version of said IFU document, and then associating said most recent electronic version of said IFU document to one or more Unique Device Identifiers (UDI).

Another embodiment of the present invention is the collaborative method for tracking and tracing a biomedical product as described above, further comprising the step of providing an indicator of whether said most recent electronic version of said IFU document has been previously accessed via said unique landing page.

Another embodiment of the present invention is the collaborative method for tracking and tracing a biomedical product as described above, further comprising the step of providing a date and time stamp of when said most recent electronic version of said IFU document was previously accessed via said unique landing page.

Another embodiment of the present invention is the collaborative method for tracking and tracing a biomedical product as described above, wherein the product is a surgical tool and the user roles of the supply-chain participants are surgeons and surgical tool distributors.

Another embodiment of the present invention is the collaborative method for tracking and tracing a biomedical product as described above, wherein the product is a drug and the user roles of the supply-chain participants are patients and pharmacies.

Another embodiment of the present invention is the collaborative method for tracking and tracing a biomedical product as described above, wherein said regulation required data comprises product safety information.

Another embodiment of the present invention is the collaborative method for tracking and tracing a biomedical product as described above, wherein said product packaging fully encloses said biomedical product.

Another embodiment of the present invention is the collaborative method for tracking and tracing a biomedical product as described above, further comprising the step of denying said scanning supply chain participant access to said supply chain participant data based on said user role rule.

Another embodiment of the present invention is the collaborative method for tracking and tracing a biomedical product as described above, further comprising the step of reconfiguring said unique landing page based on a local regulation, wherein said supply chain participant data is an indicator of said local regulation.

Accordingly, one embodiment of the present invention is a collaborative system for tracking and tracing a biomedical product utilizing data received from numerous supply-chain participants. This system comprises at least one processor for executing stored program code, at least one communication link to a connections database in a remote computer system, and at least one program memory for storing program code, operatively connected to the processor. When the stored program code is executed, it causes the processor to execute a process comprising the steps of printing, on a product packaging, regulation required data about an individual item of a biomedical product contained within said product packaging from a manufacturer, then printing, on said product packaging, a unique Quick Response (QR) code which encodes a unique Uniform Resource Locator (URL) having a one-to-one mapping with said individual item of said biomedical product, which when invoked, responds with a unique landing page showing at least said regulation required data, then receiving, via the unique URL, supply chain participant data about said individual item and a directive related to said supply chain participant data from an authorized supply chain participant, then initializing a regulation rule based on the regulation required data that governs in part how said unique landing page is presented to different users over time, then initializing a supply chain participant rule based on said supply chain participant data and said directive that governs in part how said unique landing page is presented to different users over time, then initializing a user role rule based on a user role that governs in part how said unique landing page is presented to different users over time, then receiving, via the unique URL, a scan of said unique QR code by a scanning supply chain participant, then identifying said scanning supply chain participant with said user role, and then applying said regulation rule, said supply chain participant rule, and said user role rule to present said unique landing page to said scanning supply chain participant, wherein the unique landing page is customized based at least on supply chain participant data received from one or more other supply chain participants via the unique URL.

Another embodiment of the present invention is the collaborative system for tracking and tracing a biomedical product as described above, wherein the stored program code comprises additional program code, which when executed further causes the system to perform the steps of printing an Instructions for Use (IFU) document stored with said individual item of said biomedical product, said IFU document comprising printed instructions and the unique Quick Response (QR) code, then providing a most recent electronic version of said IFU document, wherein said unique landing page is configured to redirect to said most recent electronic version of said IFU document, and then associating said most recent electronic version of said IFU document to one or more Unique Device Identifiers (UDI).

Another embodiment of the present invention is the collaborative system for tracking and tracing a biomedical product as described above, wherein the stored program code comprises additional program code, which when executed further causes the system to perform the step of providing an indicator of whether said most recent electronic version of said IFU document has been previously accessed via said unique landing page.

Another embodiment of the present invention is the collaborative system for tracking and tracing a biomedical product as described above, wherein the stored program code comprises additional program code, which when executed further causes the system to perform the step of providing a date and time stamp of when said most recent electronic version of said IFU document was previously accessed via said unique landing page.

Another embodiment of the present invention is the collaborative system for tracking and tracing a biomedical product as described above, wherein the product is a surgical tool and the user roles of the supply-chain participants are surgeons and surgical tool distributors.

Another embodiment of the present invention is the collaborative system for tracking and tracing a biomedical product as described above, wherein the product is a drug and the user roles of the supply-chain participants are patients and pharmacies.

Another embodiment of the present invention is the collaborative system for tracking and tracing a biomedical product as described above, wherein said regulation required data comprises product safety information.

Another embodiment of the present invention is the collaborative system for tracking and tracing a biomedical product as described above, wherein said product packaging fully encloses said biomedical product.

Another embodiment of the present invention is the collaborative system for tracking and tracing a biomedical product as described above, wherein the stored program code comprises additional program code, which when executed further causes the system to perform the step of denying said scanning supply chain participant access to said supply chain participant data based on said user role rule.

Another embodiment of the present invention is the collaborative system for tracking and tracing a biomedical product as described above, wherein the stored program code comprises additional program code, which when executed further causes the system to perform the step of reconfiguring said unique landing page based on a local regulation, wherein said supply chain participant data is an indicator of said local regulation.

BRIEF DESCRIPTION OF THE DRAWINGS

The invention will be understood by the following detailed description in conjunction with the accompanying drawings, wherein like reference numerals designate like structural elements, and in which.

DETAILED DESCRIPTION OF THE INVENTION

Figure 1:
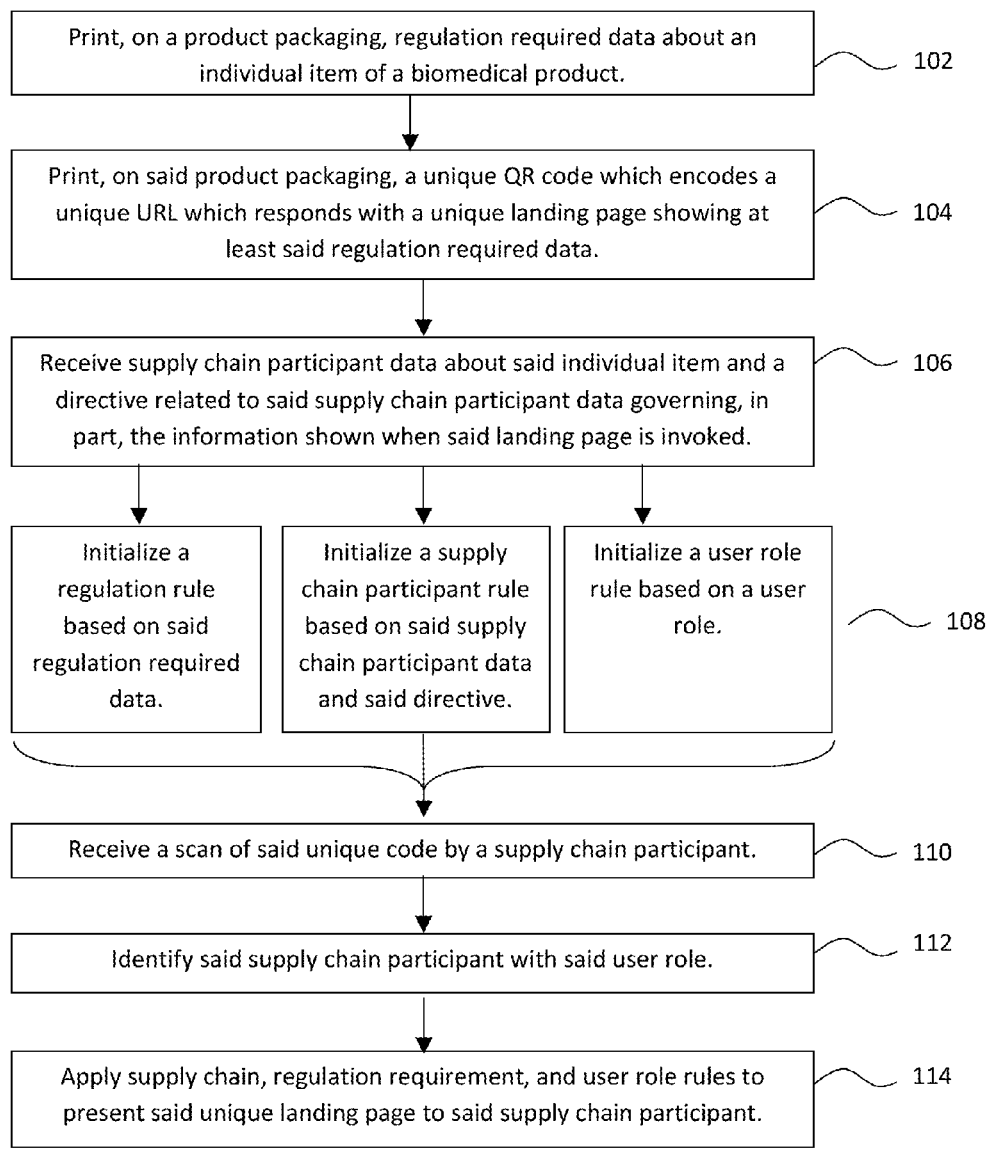
FIG. 1 is a flowchart of a method for tracking and tracing a biomedical product in such a way as to distribute relevant information to supply chain participants based on some rules, in accordance with one embodiment of the invention.

Why Track and Trace Technology is Important

Counterfeit drugs currently account for between $40B to $75B in losses for the pharmaceutical industry, projected to significantly increase as the black market evolves over the next decade, and those dollar losses do not account for the damage to public health due to these life-threatening illegitimate drugs or the societal impact of resulting increases to health care costs. The dollar losses also do not account for the damage to drug brands that causes the general public to lose faith in the products designed to restore their health. Track and trace offers the industry and consumers a method to discern between counterfeit drugs and their genuine counterparts.

Additionally, pharmaceutical track and trace benefits also include:

Track and trace as a facilitator to communication between drug supply chain participants Track and trace as a way to push active or automated updates on drug information to an end consumer, such as a recall notice or expiration notice Track and trace as an early detection system for drug package tampering Track and trace has been shown to deliver significant and tangible benefits. Examples of that which track and trace protects are: a consumer's health, manufacturer's business and jobs, brand, public health, and the affordability of health care. Track and trace has a clear potential to positively change the world we live in.

Existing Problems with Track and Trace Technology Adoption

With the FDA Amendments Act (FDAAA) of 2007, the FDA was required to create a track and trace standard for regulated products. With no implementation deadline imposed by Congress, they have not created that standard. To date, track and trace solutions have been explored independently by states and manufacturers, the best implementation having been codified in California ePedigree law. However, despite all the benefits demonstrated by existing track and trace solutions, there has been no broad market adoption of track and trace to date. This is due to the current legal and technological state of track and trace. Specifically:

Current track and trace standards, when they exist, are incompatible between states and manufacturers that implement different track and trace standards.

Based on FDA invitation for commentary in 2011, players throughout the pharmaceutical industry supply chain are divided on implementation details of any proposed federal standard for track and trace.

Because of the divided industry commentary, the FDA is itself unclear how to proceed in drafting a standard within practical merits.

Pharmaceutical companies are currently in a holding pattern in the absence of a federal regulatory standard, unwilling to commit resources to implementing track and trace solutions now in fear of future change in regulation that may render existing track and trace infrastructure obsolete and that would require expensive infrastructural change.

Existing track and trace solutions have been too restrictive to the end consumer for broad market adaptation. It is not clear to the average consumer (whose level of education varies significantly) what to do with a drug package serial number to protect their health, if they are even able to find it or know to find it.

Problems with Existing Track and Trace Technologies Themselves

The major categories of existing track and trace technologies are:

RFID—"Major pharmaceutical brands like Pfizer are leading the way with their Viagra RFID track & trace solution per bottle level across the USA" (Track & Trace Pharmaceuticals, Frost & Sullivan). Radio-frequency identification (RFID) has long been used in drug manufacturing as a way to keep track of products as they move throughout a warehouse. However, RFID has little use beyond the manufacturing warehouse as distributors and especially consumers typically lack the hardware necessary to read RFID tags, much less know what to do with the serialized string of alpha-numeric characters RFID tags encode. Furthermore, RFID is the most expensive track and trace method, with tags costing between $0.15 to $5 per drug package and their non-ubiquitous readers costing hundreds.

2D Bar Codes—"The SNI is printed in a two-dimensional (2D) data matrix bar code" (Track-and-Trace Drug Verification, NIH, 2011). A drug SNI (standard numerical identifier) is often printed on a 2D data matrix bar code, the most common type of which is a QR code. The advantage of 2D bar codes over RFID is that they are ubiquitously readable by camera-enabled smart phones and hence more accessible to supply chain parties beyond the manufacturing warehouse. However, these codes are currently being used only to store serialized strings of alpha-numeric characters and still pose the problem of being unintelligible beyond the point of manufacture.

They are problematic because they are:

Not accessible beyond point of manufacture: Hardware for reading RFID is not ubiquitous. For either RFID or 2D bar codes, the extra step of having to transcribe the raw SNI to reference elsewhere presents accessibility problems for supply chain participants beyond manufacturer.

Not intelligible beyond point of manufacture: For either RFID or 2D bar codes, the extra step of a self-directed search to reference the raw SNI presents intelligibility problems especially for less educated or underrepresented consumers. Alternative solutions to consumer intelligibility like SMS verification are cost-prohibitive for all parties.

Cost-prohibitive: Significant cost for item-level RFID tags for drug packaging, even more significant considering special hardware required. 2D bar code representations of SNI's bear significant cost whenever regulation changes, or even when drugs are shipped between jurisdictions with differing serial number standards, due to the infrastructural cost of having to change the physical codes themselves.

Low resolution tracking: The high cost of track and trace incentivizes manufacturers to use lot-level tracking instead of item-level tracking Future infrastructural changes needed: Manufacturers must change their core infrastructure and operational procedures whenever new regulation is introduced, costing millions for system hardware or software replacements alone. Enterprise software must be updated or replaced, resulting in additional consulting and integration fees.

The current technology available for identifying products on packaging tries to distill all of the relevant information into a single number, the meaning of which is not intuitively obvious, especially to the end consumer.

One embodiment of the present invention eliminates challenges posed by existing track and trace solutions by using a URL in place of a raw SNI, unique to each drug package. Each URL directs to a landing page with data specific to the associated drug, that can be updated in real time. This "smart packaging" approach is future-proof due to the technology's use of webpages that can be instantly updated to comply with current regulations. The invention allows for recalls to be managed more efficiently which not only means less liability but also less loss of human life. The invention provides immediate value to biomedical manufacturers and consumers and can benefit all supply-chain participants in the future. It provides an opportunity to scientifically understand how different users consume and share information between different points in the supply-chain.

This technology, at its core, leverages the agility and ubiquity of open web standards and mobile technology to make it cost-effective and easy for manufacturers to comply with the changing landscape of FDA track and trace regulation. No expensive infrastructural or operational changes, as the industry currently fears, are necessary for a manufacturer using the codes generated by this system and method. The ability to easily change the content and even the structure of any drug package's representative landing page to fit any new standard has significant potential to break the biomedical industry's current inertia with respect to track and trace implementation.

The web page for each drug package may include status, safety guidelines, instructions for use, or any other relevant content, accessible and understandable to the average person. Furthermore, because the URLs are printed at the item level, the information viewed by a consumer after entering the URL is tailored to that package, that batch of the product, or even, potentially, the consumer who purchased the product. A tremendous advantage the invention's generated codes have over raw serial numbers is that the manufacturer can dynamically alter the content on the web page for each drug package. In the event of a recall, for example, it would be possible to flag the pages for only the affected packages; customers scan the QR codes to see if their particular product is affected.

For the purposes of this patent, the adjective biomedical is used to describe anything of or relating to biology and/or medicine. Biomedical products might be any items used by doctors or patients for the purpose of promoting health and wellness, and may include chemical compounds used to treat or prevent illness, i.e. drugs and other biomedical products, as well as instruments or objects used in the course of practicing medicine, e.g. surgical devices, diagnostic hardware.

In the biomedical industry, track and trace refers to the process of determining the current and past locations of drug or medical device products. The location of a product can mean either a physical geo-location or the part of the supply chain the product has been or is currently being handled in. Specifically, tracking refers to knowing the current location of a product and anticipating its future destination(s), while tracing refers to recording and being able to retrieve the previous locations a product has been in or passed through. Track and trace processes often generate an e-Pedigree for a product, which is defined as an electronic document containing all of the information necessary for a drug pedigree. A drug pedigree is defined by the FDA as "a statement of origin that identifies each prior sale, purchase, or trade of a drug, including the dates of those transactions and the names and addresses of all parties to them" (71 FR 66448). For the purpose of this patent, it is useful to consider an e-Pedigree to be the electronic document recording the passage of the product through the supply chain. The term supply chain refers to all entities responsible for getting the product from its point of manufacture to its point of use or consumption, including but not limited to the manufacturer and consumer.

Product authenticity information refers to any data indicative of a product's identification at any level, whether it is the item level (package level), batch level, group level, product level, product type level, product classification level, etc. An example of an item level identification for a product is the Serialized Numerical Identifier (SNI) as defined by the FDA for drug packages. The SNI is one way to provide a unique drug identification at the level of a saleable unit. Another example of an item level identification is the Electronic Product Code (EPC) as defined by EPCglobal, Inc. Another example of an item level identification is the Unique Device Idenfier (UDI) as defined by the FDA for medical devices. The SNI, EPC, or UDI are just few of many ways to provide a unique drug or medical device identification. An example of a product level identification is the National Drug Code (NDC), also as defined by the FDA. Another example of a product level identification is the Global Trade Identification Number (GTIN) as defined by GS1. An example of a product type level identification is the Stock-Keeping Unit (SKU) as widely used in industry.

Product safety information refers to any data indicative of precautionary step communicated to the consumer by the manufacturer, other supply-chain participant or other organization, comprising risks in product usage, hazards, potential side effects, disposal, potential risk factors for diseases associated with the product, etc. An example of this would be a warning such as "keep away from children under 5" or "do not take if you are pregnant." Such product safety information can originate from any supply-chain participant or third parties such as a government agency, grassroots organization, etc. Examples of organizations that have a mission for public safety and may issue notices are the United States Consumer Product Safety Commission, Occupational Safety and Health Administration (OSHA), the Surgeon General, the American Public Health Association (APHA), etc. Product safety information may also include actionable directives such as "Contact your healthcare professional if you experience asphyxiation after using this drug."

Regulation required data refers to product data that is required by regulatory guidelines from regulatory agencies that regulate the product in question. Examples of regulatory agencies are the Food and Drug Administration (FDA), Federal Trade Commission (FTC), Federal Communications Commission (FCC). Regulation required data may also include reference to whichever agency or the legal code that governs the necessity of the data presented. Examples of product data that fall under regulation required data are a Serialized Numerical Identifier (SNI) for drug packages as instructed by the FDA or a Unique Device Identifier (UDI) for medical devices as instructed by the FDA. Another example of product data that is required by the specific state jurisdiction of California is a drug product's e-Pedigree, as defined by the California Department of Consumer Affairs, Board of Pharmacy.

Individually unique QR codes that encode a unique URL directing to an individual landing page may be printed on external packaging of a biomedical product, such as paperboard packaging or a bottle. It may also be printed on an Instructions For Use (IFU) document, safety instruction document, product manual, legal disclaimer, or any other type of media that accompanies or is contained in packaging.

Unique links are distinct references to an Internet resource, which are commonly called uniform resource locators (URL's). Unique links can be represented in many different forms but the most typical form is a character string that follows some translatable pattern (most commonly "scheme://domain:port/path?query_string#fragment_id"). Unique links could also be represented as two-dimensional image such as a quick response code (QR code). Any other form of representing a reference to an Internet resource is contemplated under the definition of a unique link. Unique links can also be represented in shortened form using various URL-shortening techniques. For example, one URL-shortening technique is to apply a hashing function to a long URL to generate a six-character hashing result string. The resultant string then forms a new URL in conjunction with a shortened domain whose function is to maintain a database of long URL's and their shortened forms and perform forwarding operations in response to web server requests.

One aspect of the invention relates to the process of generating unique links. Various methods can be used to generate unique links. For example, within the example domain "doma.in" a unique link may look like "doma.in/j30gje" and another may look like "doma.in/h5j29e." The subdomain segment of an URL may also be used, such as "398tj2.domain.com" or "hg84h4.domain.com." In the example case of "doma.in/j30gje", the last six characters represent the distinguishably unique segment of the unique link. One example way to generate these characters is to implement a random generator of 6-character alphanumeric strings. Another way to generate these characters is to build a hash function that takes as input some content related to the destination of the URL and maps it to the space of 6-character alphanumeric strings. For example, one could apply a hashing function to the title of the destination web page to generate a unique link. Another possible way to generate unique links is to use a simple alphanumeric system and provision the URL extensions in alphanumeric order. One example of this is a pure sequential numeric generator that outputs "000", "001", "002", "003", "004", . . . , "999" in succession. Another example of this is a sequential alphabetic generator that outputs "aaa", "aab", "aac", "aad", . . . , "zzz" in succession. Yet another example of this is a sequential alphanumeric generator that outputs "aaa000", "aaa001", . . . , "zzz999" in succession. Yet another example of this may also employ the use of a hierarchy of base folders, such as "john/aaa001", "john/aaa002", . . . , "peter/zzz999" in succession. One of skill in the art will recognize that these methods can be modified or combined to produce other valid schemes for unique URL generation within a domain.

Depending on the technique used, there may be variations in the number of possible unique links that can be generated, variations in the quality of the unique links generated, or variations in the number of collisions of unique links generated. If a larger space of possible unique links is desired, the limitation of 6 characters can be lifted to allow any variable number of characters. For example, if instead an implementation of 32 alphanumeric characters is used instead of 6 alphanumeric characters, the space of possible unique links would grow from $62^6$ (56 billion permutations) to $62^{32}$ ($2.27 \times 10^{57}$ permutations). The quality of unique links generated can be determined based on factors that affect the use case. For example, if the use case is such that unique links are being generated for people to recall from memory, the quality of the unique links generated would positively trend with its simplicity. In that particular case, a randomly-generated 6-character alphanumeric string would be considered a low-quality unique link, whereby a sequentially-generated 3-character alphanumeric string ("000", "001", . . . , "ZZZ") would be considered a high-quality unique link. Invariably, a technique that is engineered to generate high quality unique links may also be more limiting in the space of possible unique links. As applied to the last example, for the 3-character alphanumeric string technique (a high-quality technique for the use case of memory recall) the space of possible unique links is $62^3$ (only 238,328 permutations), whereby for the 6-character alphanumeric string technique (a low-quality technique for the given use case) the space of possible unique links is $62^6$ (56 billion permutations). Finally, it is noted that another variable in generating unique links is the collision probability. This variable is especially relevant in certain use cases in which generating unique links must be fast and frequent. As in any application of hashing functions, one of the most important qualities of a hashing function is the minimization of its collision frequency. In the examples previously cited, the sequentially-generated 3-character alphanumeric string method's collision frequency is 0 because by virtue of being sequentially generated, the generator simply increments the most recently generated string by one and guarantee no collision. If using a hashing function on some destination content, the collision frequency simply approaches the collision frequency of the hashing function itself. If using a random 6-character alphanumeric generator, for example, collision frequency would approach $1/62^6$.

Mobile devices include iPhone, Android, Blackberry, a digital camera like the Sony Cybershot, Panasonic Lumix, Nikon Coolpix, Casio Exilim, Canon Powershot, a mobile tablet like the iPad, a mobile industrial device like the Motorola MC75 or Psion Teklogix, or any personal computer. One of skill in the art will recognize that there are many other possible devices, all of which fall within the scope of this invention. A mobile computing device is most effective if it is able to electromagnetically communicate with other devices over a network. Means to communicate electromagnetically with other devices may include wired communication, such as sending electromagnetic signals through Ethernet wire, coaxial cable wire, fiber optic wire, copper wire, platinum wires, and the like; wireless communication, such as sending radio signals, visible light, laser, gamma rays, x-rays, micro-waves, ultraviolet waves, and the like. The communication may follow one or more protocols of communication, protocols that include but are not limited to TCP/IP, UDP, ICMP, IMAP, SMTP, FTP, HTTP, or HTTPS. Being "network-enabled" typically means being able to communicate with one or more other devices that are able to interpret the communication protocols that the digital media capture device use. The computing device is also most effective if it is able to communicate with one or more databases. A database could be contained within the computing device itself as a component, or it could be a remote database that the computing device communicates with using any of the electromagnetic communications means described above. A database, for the purposes of understanding this invention, should be able to persist data representing connections and its meta data. It may use conventional database engines to handle and query the persisted data, such as by using MySQL, POSTGRES, Sybase, Sqlite, Oracle or other such database engines.

One aspect of the invention relates to a system for managing the destinations of unique connections. A connection is a data structure that manages at least one landing page and directs or routes visitors to one or more landing pages. The connection may direct a recipient user to a landing page set up by another user of the system to serve relevant content to that recipient user. Landing pages may be "owned" by the connection in a one-to-one relationship, or a connection could own more than one landing page in a one-to-many relationship. Any given landing page could also be shared between multiple connections in a many-to-many relationship. Each connection may be configurable through a computer-implemented interface. The purpose of the connection may, for example, be for a manufacturer to send a recall notice to an end consumer. The data published can be a text note, a date/time stamp, a geo-location, a combination of these or other such content that is used to capture the circumstances of a situation like that. It could, for example, be a date and time stamp of when the most recent electronic version of an IFU document was previously accessed via a unique landing page.

One aspect of the invention relates to setting up a default landing page for a connection. The connection can direct a visitor to the default landing page as its primary function. This can be accomplished by storing in a database the location of a default landing page that is owned and editable by the user of the system who also owns the connection. The default landing page can, for example, allow the owning user to post information about the associated product that is typically posted to the product website. It could also contain links to web documents hosted at other sites as well, such as a vendor's, giving the landing page an aggregation role and serving as a directory of the associated product's web presence.

One aspect of the invention relates to re-configuring connections to direct a visitor to content located elsewhere. The content can be stored at and retrieved from another location on the Internet, or stored and retrieved locally on the computing device on which the system resides. The re-configuration of connections to point a visitor elsewhere can be achieved through a connection management interface whereby a user of the system can select a connection to edit and specify an override to the ultimate destination of the connection. The system can achieve the override through various methods such as URL redirection in a web application, server redirection, domain forwarding, etc.

One aspect of the invention relates to counting clicks for connections. A click is any single instance of a visitation to the connection. Click counting can be implemented on the application level whereby a connection resource request causes a subroutine to be executed in which an integer stored in the database and related to the owning user of the connection is incremented. It could also be implemented at the web server level, whereby a server log of requests to a particular resource of an owning user is aggregated and counted.

One aspect of the invention relates to adding digital content to a unique landing page for a visitor. Digital content means any content in computer-readable format such as photo files, video files, audio files, text document files, text messages, screenshots, scripts, computer programs, news articles, gossip, blog posts, podcasts, forums, reviews, research articles, research publications, wikis, animations, games, game player-generated content, digital security certificates, and other such content.

One aspect of the invention relates to controlling privacy of the content associated with a connection. One way this could be implemented is by blocking access to all of the connection's content.

The invention for pharmaceutical track and trace includes the step of creating and deploying unique links on printed media (i.e. an item-level QR web link on drug packaging) which when scanned, directs to a landing page serving as an actionable data component in lieu of an inert serial number. The technology may be implemented at the packaging and printing manufacturer point in the drug supply chain, to be used throughout the rest of the supply chain. The invention is best integrated into a manufacturer's operations and calibrated to achieve a production throughput that at least matches the manufacturer's existing operational throughput for the direct printing of Standardized Numerical Identifiers (SNIs) for biomedical packages. To achieve this, the manufacturer must set up a device or system of devices to be able to (a) generate unique codes and initialize legally required data associated with each individual code that is related to the individual biomedical package to which it has been assigned. Additionally, the manufacturer must have computing capability for the system to be able to (b) update any of the data in real time in response to changes in drug status. Both steps (a) and (b) must be able to keep up with the manufacturer's rate of production and rate of updating. For example, a drug manufacturer may process 1000 drug packages per minute at the facility, so the system should be calibrated to handle that throughput.

To generate and initialize codes at a speed that meets manufacturing throughput expectations (at mass scale), a code initiator software component is written to do the following:

Expose a REST HTTP web service API that can retrieve and write data in reference to the code for a particular drug package, with the following functional endpoints implemented:
Create new code (returns CodeID)
Add {key:value} data pair to code identified by CodeID
Retrieve data from code identified by CodeID, given a key
Create new package image template (returns PackImageID)
Retrieve coded package image, given a CodeID and PackImageID
Initialize the code with at least the following information:
　Serial number such as FDA standard numerical identifiers (SNI)
　Batch/lot number
　Expiration date
　Packing date
　Supply chain e-Pedigree
　Product recall information (current status, date/time of recall, where to return the product, why it is being recalled, associated warnings/disclaimers)

One factor that is important is the amount of time it takes from the start of code generation to the end of the initialization process (a full cycle of code generation/initialization), as this directly affects the performance of an actual manufacturing production run. Calls to each API function can be benchmarked on throughput and full cycle time performance along the axes of available network speed, memory, processor speed, and other possible factors that directly or indirectly affect throughput and roundtrip time. If a manufacturer has a particular throughput or roundtrip time requirement that is not reached via benchmarking of the system, one of skill in the art would recognize that various increases or combinations of increases in network speed, bandwidth, parallel processing, etc. can be made to achieve the manufacturing goal. Other optimizations may be introduced such as compressing data that is being sent through a network and decompressing at the destination.

Throughput and concurrency of code generation/initialization on the manufacturing floor are two major factors. One embodiment of the present invention may comprise storing and sending high-resolution images to printing machinery at a packaging manufacturer, and have it make HTTP requests to a code initiator software component, and then receive text and image data responses. Iterative HTTP requests can be made to get uniquely coded package images for the quantity of packages to be printed that day. Since quantity generally changes per job, the system should be calibrated to support the range of quantities expected.

For efficient updating, codes can be grouped logically for mass scale publishing actions at varying levels of granularity. Granularity is taken to mean the specificity at which a set of codes (unique at the drug package level) is required to be updated, such as batch level (ex. "all drug packages belonging to batch JN1294") or package level (ex. "drug package with CodeID 3985395") or even advanced groups (ex. "all drug packages belonging to batch JE3511 with pack date >Dec. 1, 2012 that has distributor XYZ in its ePedigree"). A code updater software component can, in addition to offering the base functions necessary to update any individual drug package code's associated landing page, bulk update millions of those drug packages in real time with a given granularity. Granularity is determined by the manufacturer based on the update situation (such as emergency drug recall) so the code updater software should be architected to deal with granularity as a random variable. The usage of a rules engine that can integrate with workflow and event processing (such as JBoss Drools) is strongly recommended as an implementation strategy for the code updater, so that granularity can be best expressed as a rules set. Performance can be measured on the minimization of time to implement a full set of updates to in-circulation codes for a diverse range of granularity configurations. Performance vs. granularity level should be profiled, and can be iteratively optimized by rewriting rules and re-indexing data.

A platform capable of carrying out actions on the system by supply-chain participants is any smartphone, such as an Apple iPhone with a QR reader application communicating. It is actually possible for all actions in the system to be carried out by a smartphone device, however, due to the possible heavy loads in practical manufacturing environments, the system is best implemented as a distributed network of devices, with a server machine with dedicated RAM running a network-enabled operating system and a web server centrally. An example of such a central server may be a Linode server with dedicated RAM running a Fedora Linux instance with an Apache web server. The central server may be local or remote. An example of a distributed system of devices may be the central server as described, deployed at a manufacturing facility, communicating with one or more smartphone devices being used to scan individual codes on biomedical packages that are processed at the facility.

Finally, one of skill in the art will recognize that there may be security issues involved with having codes in circulation, where anyone can scan the content code and interact with content intended only for the recipient to interact with. This problem can be curbed by the introduction of a security layer, such as a public or private key system or perhaps by authenticating a text password that is already known to the recipient, perhaps through a pharmacy receipt or other handshake data.

Social Construction of Item-Level Biomedical Information

The rule of law codifies our societal duties and obligations to one another. This invention recognizes the social responsibilities that manufacturers have to consumers and that pharmacies and biomedical retailers have to patients. This invention allows these parties to socially construct an individual landing page to fulfill these social aims. In this invention, the social dynamics of these relationships between manufacturers, supply chain participants and patients have corresponding read/write capabilities. Manufacturers publish information on the page which is legally required (e.g. UDI, Lot or Batch number, expiration date, manufacturing origin) and track product distribution. Pharmacies use the landing page to publish information to ensure safety, offer additional wellness services, and track patient use. Patients use the landing page to publish feedback on how their use of products affects them so that it can be anonymized and provided to manufacturers for use in improving products and can read safety notices such as product expiration or recall.

Product recalls happen every year in the United States and often there can be deadly consequences when recalls are not initiated and effectuated expediently enough. In October 2012, New England Compounding Center and a company with the same management, Ameridose, issued a recall of all of its products because their contaminated products cause 404 people to be infected with fungal meningitis. Twenty-nine of those infected died. It was the diligent work of Public Health officials in Tennessee that initially traced the source of the meningitis outbreak to the New England Compounding Center. This is one recent example of how recalls have not only significant financial costs but also have societal costs ranging from decreased consumer confidence to truly grave matters like loss of human life.

Manufacturers can use this invention to micro target recalls to specific, affected products by publishing that information to the product's landing page, other supply chain participants, like retailers and pharmacies, will receive notice of a recall and see which customers have been affected, customers become instantly aware of whether their product is affected by the recall provided the scanning supply chain participant has provided their contact information to their pharmacy. An example of this would be where a drug manufacturer becomes aware that Lot #5 of Product X has been contaminated. They use the system to change the landing page to show a recall notice for all URLs which cover a product from the contaminated Lot #5. A pharmacy which uses the system as a downstream supply chain participant has its own protocols for managing recalls of products it sells. Those protocols are embodied as rules in the system which generate a list of the patient numbers who have received a unit from Lot #5. The pharmacy imports those patient numbers into its system where it allows them to see the contact information for each affected customer. The pharmacy can use the system to track if it has been accessed or record if they have already reached the customer by phone. The patient scans the card to get information on what they should do with the product, what they should be aware of and receive any other critically important information about the recall and can use it as a way to communicate back to their pharmacy. This technology will make recalls more efficient and safe.

In FIG. 1, a flowchart 100 illustrates the sequential implementation of one embodiment of the invention. The initial steps, 102 and 104, involve printing unique data on biomedical product packaging, including at least regulation required data. Regulation required data might include anything the FDA or other branches of the federal government, state governments, or the industry mandates must be made available to consumers of the biomedical product, such as the Unique Device Identifier (UDI) number, expiration date, warnings, or instructions for use of the product.

Step 106 deals with obtaining information from supply chain parties which may include the manufacturer, wholesaler, distributor, consumer, or other entities that participate in handling or processing of a product. This information may be related to one or more individual products, and may be collected at any time after the point of manufacture.

In the row labeled 108, three distinct steps are shown, which may happen subsequently or simultaneously with each other. All of these steps initialize a rule based on some information gathered in previous steps.

Regulation rules are those based on the required regulation data. A regulation rule might be, "If this item is past its expiration date, display a red warning alerting users that it is expired." Regulation rules would also include displaying recall notices if an item had been recalled.

Supply chain participant rules are those based on supply chain participant data. An example of supply chain participant data is a recall notice posted by a manufacturer. In this case, the manufacturer would input into the system a data item representing the details of the recall notice (such as date/time of recall, affected batches, severity level of the recall, etc). The system would then take this data and create a supply chain participant rule which could be, for example, "If the drug package is part of any of batches 1003, 1005, or 1009, display in large font and in bright red the word RECALL, along with the directive to bring the package back to the pharmacy from which it was obtained." The supply chain participant rule could be a more complicated rule, that references and/or subdivides parts of the supply chain participant data. It can even construct a directive using the specific parameters of the drug package, such as "If drug package is part of any of batches 1003, 1005, or 1009, display in bright red 'Your package {serial_no} is now being RECALLED because it is part of batch {batch_no} '," in order to provide more specific information through the landing page for the viewer. The supply chain participant rule can be constructed using a conjunction of supply chain participant data, regulation required data, and user role data. It can even take into account other external data (such as from a third party database) and even situational data such as current date/time or landing page viewer geo-location. The supply chain participant data can come from any supply chain participant, including but not limited to manufacturer, wholesaler, distributor, and even the consumer, via writing to the landing page interface or through a corresponding landing page API. Hence the supply chain participant rule can be based on data that comes from any player or user role within the supply chain.

User role rules are based on the user role of the scanning supply chain participant who will scan the QR code in step 110. These rules allow two users to see different information or have different permissions to modify the same product. For instance, a user identified as the product manufacturer might have the option to update the product instructions for use, or to issue a recall, but might not be shown where the item was purchased; a consumer, on the other hand, might have the option of answering questions on his or her experience with the product, but would not be able to issue a recall. A distributor might be shown more or less of the product's ePedigree than the consumer or the manufacturer.

In step 112, the supply chain participant who scans the QR code is identified with some user role. This can be done via a login or lack thereof; some users might be required to have user data stored to authenticate their permissions, whereas other users might be allowed anonymous access to some limited version of the landing page.

Finally, in step 114, the regulation requirement rule, supply chain participant rule, and user role rules are all applied, either serially or in parallel, to shaping the content and structure of the landing page that is viewed by the scanning supply chain participant.

Figure 2:
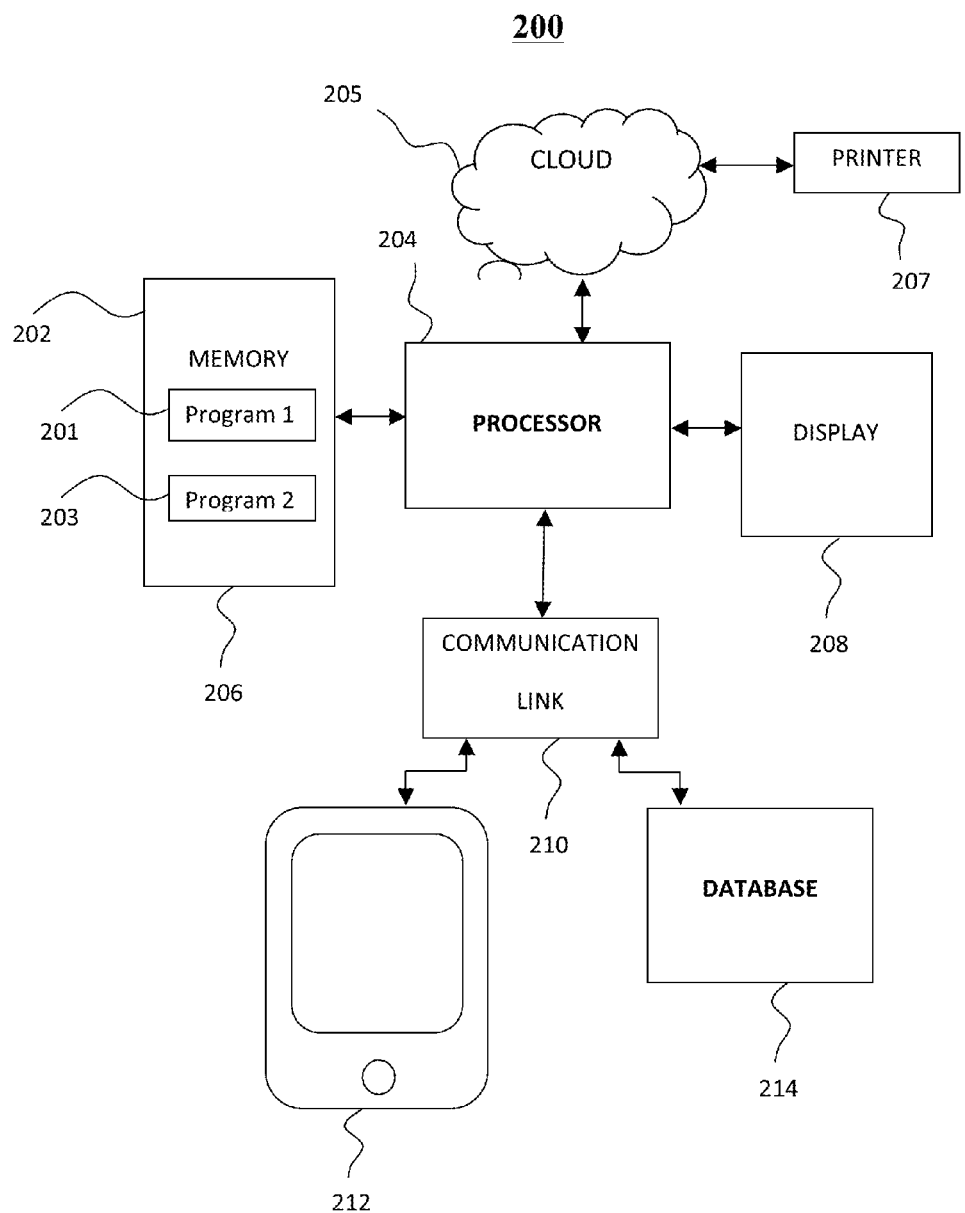
FIG. 2 is a block diagram of a system for tracking and tracing a biomedical product, in accordance with one embodiment of the invention.

FIG. 2 is a block diagram of an exemplary system 200 for receiving and distributing product information to members of the supply chain, in accordance with one embodiment of the present invention. The system 200 may correspond to but is not limited to being a computer system such as a desktop, laptop, tablet PC, handheld mobile device and the like. The system 200 includes a central processor 204, a memory unit 202 which loads one or more programs, 201 and 203, network cloud 205, a printer 207, a display 208, a communication link 210, a device capable of scanning a QR code and sending and/or retrieving information 212, and a database for storing product information 214.

When the system is in operation, the memory unit 202 is loaded with one or more routines. While the system is in operation, data can be loaded into this memory unit 202 ad-hoc, perhaps as a result of a data caching operation or other operation that requires such placement of data.

The processor 204 is a hardware component configured to execute instructions and carry out operations associated with computer system 200. Examples of such a processor could be a CPU of any architecture (CISC, RISC, EDGE, 8-bit, 32-bit, 64-bit, etc.), a combination of CPU's of any architecture performing operations in parallel, a combination of specialized CPU's such as a microcontroller coupled with a digital signal processor, the hardware of which is efficiently designed to process certain signals (such as graphics in a GPU), or perhaps a vector processor, or any other processing device that can carry out the task of executing instructions and carrying out operations associated with verification system 200.

The communications link 210 can be any method of exchanging data between the processor, the database, and the receiving device, including but not limited to a physical connection, a wireless network connection, 3G, 4G, a cloud service, or a virtual communication link, such as between host operating system and virtual operating system. Network communication is achieved by connecting the processor 204 to network cloud 205. The processor is then able to communicate with remote printer 207. One of ordinary skill in the art will appreciate that the network cloud could be implemented in the same way as communications link 210. Additionally, it could include an implementation of internal procedures for how to deal with manufacturing hardware, such as a printer. The printer 207 is representative of industrial-grade hardware that is instructed by the processor 204—protocols for sending printer instructions comprise HTTP, LPT, FTP, or other such ways to communicate with industrial printing machinery.

The database 214 is any unit capable of storing, sharing, and updating product information, including identification and authentication information and the e-Pedigree information generated as the product moves through the supply chain. The data may be stored in any structure; some possibilities include a relational database, e.g. SAP, Oracle, MySQL, PostgreSQL, IBM DB2, Microsoft SQL Server, SQLite; a NoSQL database such as MongoDB; or writable files in a file system.

Figure 3:
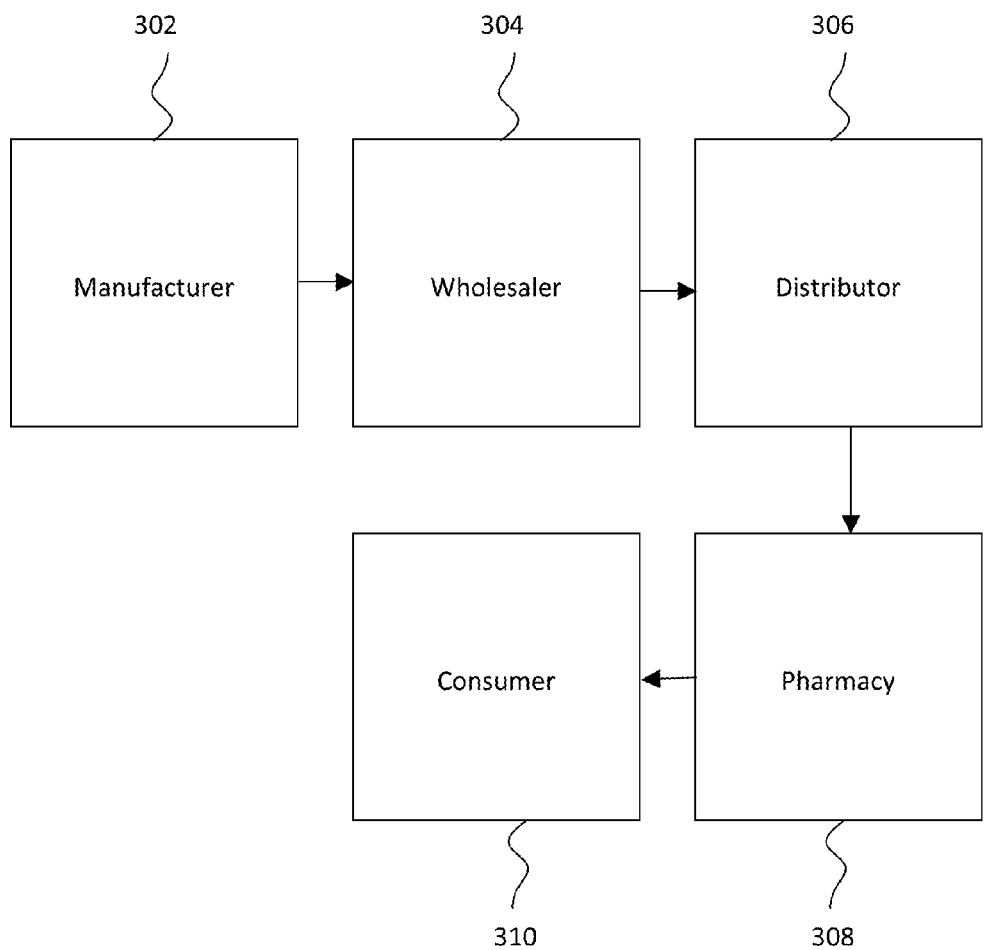
FIG. 3 is a flowchart illustrating a potential supply chain for biomedical products, including supply chain participants.

FIG. 3 shows a potential supply chain for the distribution of biomedical products. The manufacturer (302) is defined as the entity which creates the product, and the consumer (310) is the entity which ultimately uses the product for its intended purpose. The consumer may be someone uninvolved in the medical profession who purchases over the counter or prescription drugs; the consumer may also be a doctor, surgeon, or other medical professional who uses a biomedical product to diagnose or treat a patient. In the interim steps between the manufacturer and the consumer, other entities may participate. Some entities which may involve themselves in the supply chain include, but are not limited to: a wholesaler (304), who purchases the product directly from the manufacturer; one or more distributors (306), who transport the product; and a pharmacy (308) or other retail store, where consumers are able to purchase the product. The consumer could be a patient who has a prescription for a drug to pick up at a pharmacy, staff at a hospital (such as a surgeon) that regularly procure supplies for usage in the emergency room (such as surgical tools), etc. The invention can accommodate an arbitrary number of participants in the supply chain, with each potentially having their own qualifications, allowing them to view unique information on the product upon scanning the code printed on the product.

Figure 4:
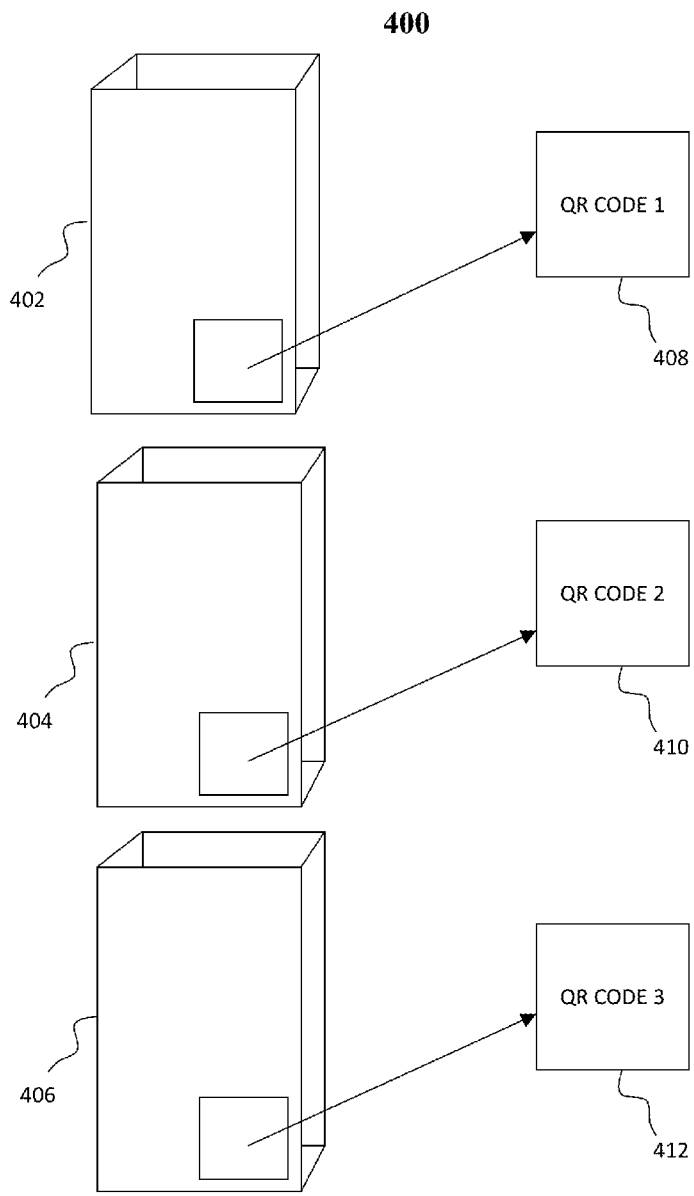
FIG. 4 is an illustration showing three otherwise identical packages of a single biomedical product have each been printed with a unique barcode.

FIG. 4 shows three different packages of the same product. 402, 404, and 406 are functionally identical, each containing the same quantity of the same product and having the same branding, etc. The only difference lies in 408, 410, and 412, three unique QR codes printed on the respective packages. Like 1D barcodes or ID numbers printed on packages, each QR code is an item-level identifier of the package.

In one embodiment of the invention, each of 408, 410, and 412 encode a unique Uniform Resource Locator (URL), each of which references a unique landing page for the individual package the code/URL correspond to, creating a one-to-one connection between the consumer who purchased the product and the other members of the supply chain.

Figure 5:
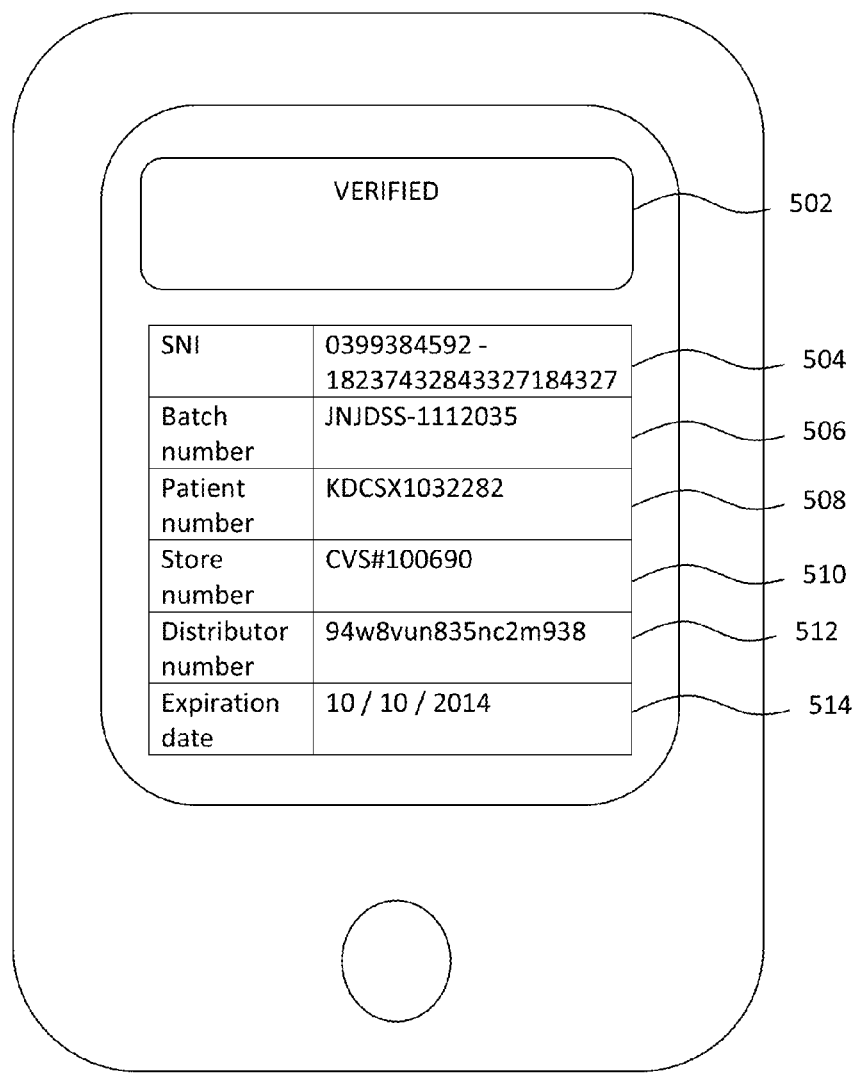
FIG. 5 is an example of an item-level web page which might be displayed for a customer upon scanning a QR code on a biomedical product.

FIG. 5 shows an example of a landing page a customer might view upon scanning the unique code, including dynamic content and identifying information.

502 is one or more pieces of dynamic content. Dynamic content is defined as information which might be changed after the sale of the product, by the manufacturer or by some other entity involved in the supply chain, and which might vary depending on the credentials of the user viewing it, i.e. between a consumer who scans the code and a distributor who scans the code.

In a case where the invention was being used for anti-counterfeiting measures, the dynamic content might say 'verified' if the product met the requirements to establish it was not counterfeit, or 'warning' if the product did not meet these requirements. 502 might also display further information on how the verification was established, or, if the verification was not established, information on actions the consumer could take in regards to their counterfeit product. In a case where the invention was being used in a recall situation, location 502 might display 'safe' if the product was not part of a recalled batch or 'recalled' if the product were part of a recalled batch. 502 might display further information on where to return the product if it was recalled. In a case where the invention was being used to track that the instructions for use (IFU) for a product had been read, 502 might read 'not read' if the user had not viewed the IFU since the publication of the latest version or 'read' if the user had viewed the most current version of the IFU.

The dynamic content displayed might vary for individual instances of the same product. It might also vary based on the credentials of the person accessing the page, i.e. the manufacturer might see an option to place a recall while the consumer sees only whether it has been recalled or not.

In the event that the dynamic content on a product landing page displays actionable information, e.g. that the product is counterfeit, a recall has been placed on the products, or the IFU for the product has not been read by the consumer, the manufacturer could supply a recommended action for the user to take. This could take the form of a text note, link, button, etc. For example, in a recall situation, the dynamic content may indicate where the consumer can return the product to get a replacement or refund; in a counterfeit situation, the consumer may be given a phone number or email to report the counterfeit product to; or in a situation where an updated IFU has been published, the consumer may be provided with a link to the most recent IFU.

504, 506, 508, 510, 512, and 514 are pieces of static identifying information which may vary between products. Identifying information is defined as information which is specific to an item but should not change after the sale of the product. Identifying information might include product authenticity information (504), which is defined as information unique to the item, e.g. a Standardized Numerical Identifier (SNI), National Drug Code (NDC), or a code assigned based on an inter-industry numerical standard such as SKU, GTIN, or UPD. Identifying information might also include grouping information (506). Grouping information is information used to relate this item to other instances of the same product, e.g. a lot number or a batch number. Identifying information might also include information from the ePedigree of the item in question (508, 510, 512) about its journey through the supply chain. Information from the ePedigree might include some manner of identifying the consumer who purchased the product, the store at which the product was sold, the distributor who provided the product to the store, etc. Information from the ePedigree might also include information on when the product was transitioned between members of the supply chain, e.g. placed in retail outlet by distributor, purchased by customer from retail outlet. Identifying information might also include safety information known at the time of manufacture, such as the expiration date of the product.

Every landing page which has a URL encoded in one of the QR codes printed on some piece of packaging can potentially include both dynamic content and ID info.

Figure 6:
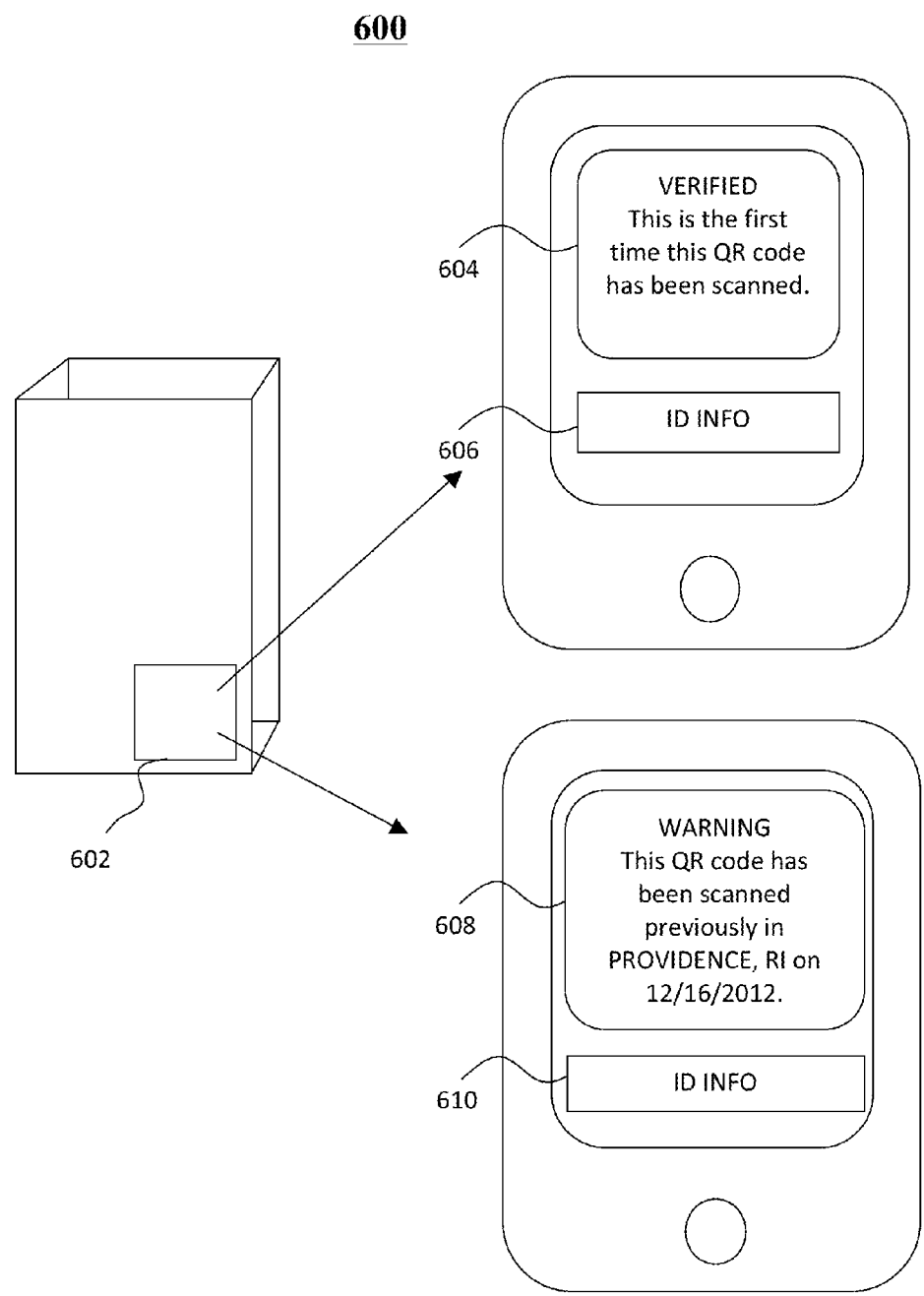
FIG. 6 is an illustration of two potential outcomes of product authentication by scanning a QR code printed on the product package.

FIG. 6 shows a potential implementation of the invention for anti-counterfeiting purposes. In this embodiment, the QR code is printed on the inside of the packaging and cannot be accessed without obviously tampering with the package. Upon opening a package, the consumer scans the QR code (602) with a smart phone, tablet, or other appropriate device. The system records that the code has been scanned, what entity along the supply chain has scanned it, and where the device that scanned it was located at the time of the scanning. If the code has never been scanned before, that implies that this package has never been opened by a consumer and that no duplicates of this code exist. The landing page might therefore display some dynamic content similar to 604. If, however, this code has previously been scanned by a consumer, the landing page might display dynamic content as in 608, with an alert that this product might be counterfeit, along with the date and location of the previous scan. The consumer can use this information to authenticate their product. If the date and location match with a previous scan that the consumer performed, then the product is still safe to use. If, however, the consumer knows that she/he never scanned the code before, or did not scan it at the listed time or location, then there must be a duplicate instance of the code, and this product is therefore not being distributed through the proper channels. The dynamic content in 608 might also include instructions on where to report or return counterfeit products.

In this embodiment of the invention, the identification information (606 and 610), which might include an SNI number, batch number, expiration date, etc., is displayed on the landing page regardless of whether the product is marked safe or bears a counterfeit warning.

Figure 7:
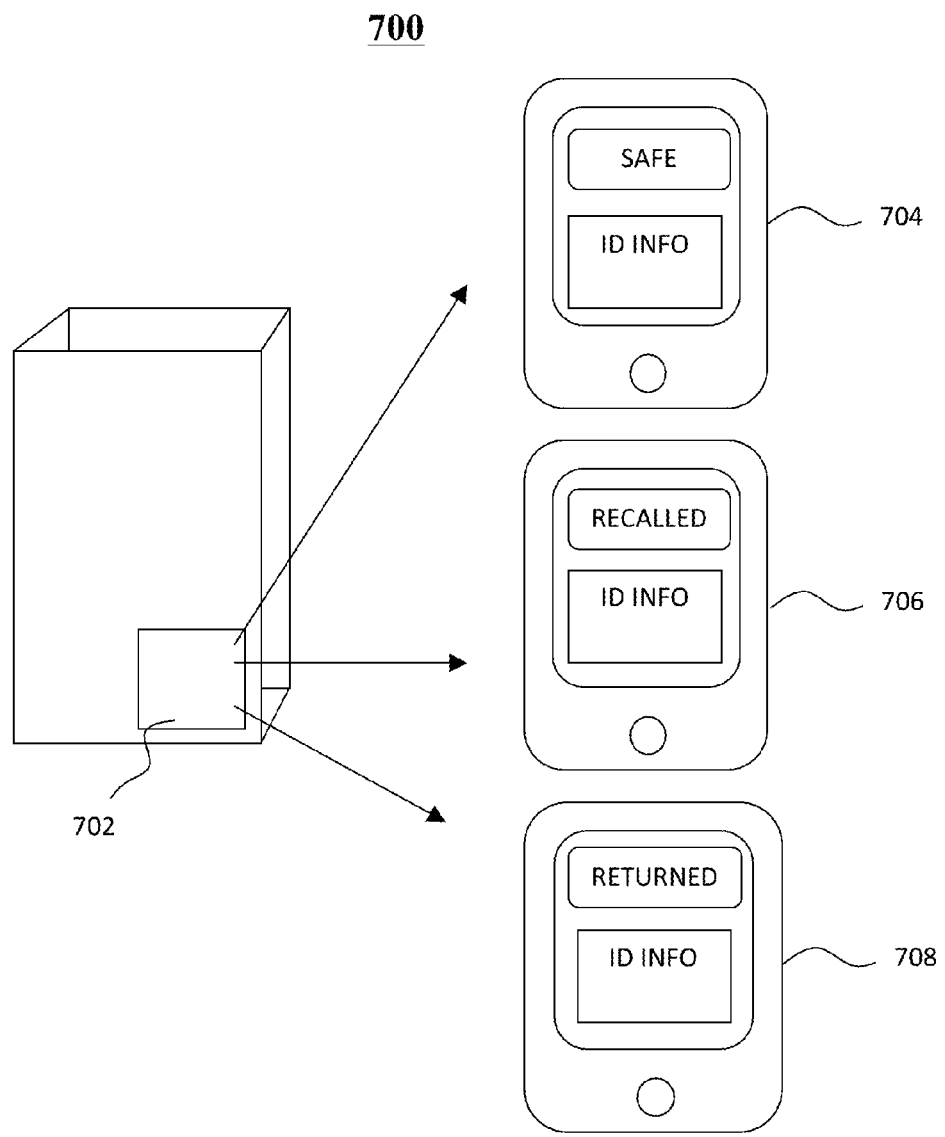
FIG. 7 is an illustration of an item-level QR code being used by both customers and manufacturers in a recall situation.

FIG. 7 shows a potential implementation of the invention in a recall situation. A recall would be placed by the manufacturer on certain groups of the product, which would be defined by some predetermined sorting method such as lots, batches, date of production, etc. Consumers would then scan the unique QR code (702) on their product packages using a smart phone, tablet, or other appropriate device to view the landing page for their product. 704 shows an instance where the product is not part of the affected group. The dynamic content would display an alert informing the consumer that the product is safe to use. 706 shows an instance where the product is part of the affected group. In this case, the dynamic content would display an alert to inform the consumer that the product they have is part of the recall. It might also include information on where the product should be returned to if a refund or replacement is being offered.

A recall situation might also take advantage of other members of the supply chain to manage the return of recalled products. For instance, a pharmacist or distributor receiving product returns might scan the codes of said products and mark them as 'returned,' making it easier to track the number of recalled items still on shelves or in the hands of consumers. A manufacturer, accessing the landing page for an item through that item's QR code or through their own database, might see an alert such as in 708, informing them that the item has been returned.

Figure 8:
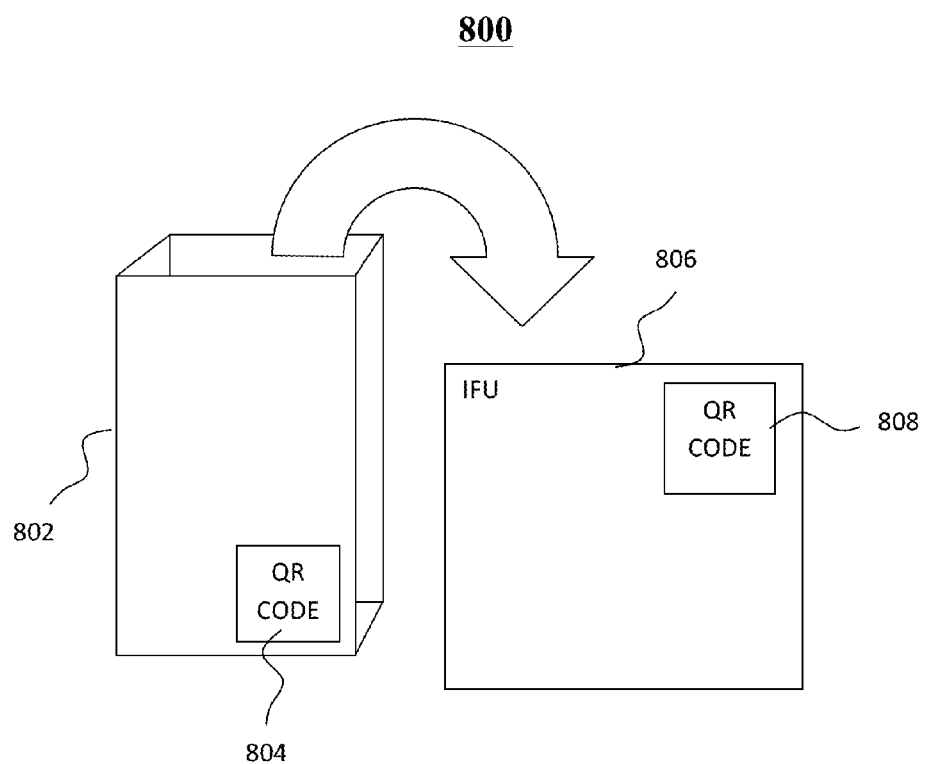
FIG. 8 is an illustration of interior packaging, i.e. product IFU, being marked with the same QR code as the product package.

In some embodiments of the invention, the QR code might be printed in multiple places on the packaging. FIG. 8 demonstrates this. QR code 804 is located on the outer packaging, while 808, an identical QR code, is printed on the product's interior packaging material. The outer packaging is defined as anything visible without opening or tampering with a package, e.g. paperboard, bottle, box, foil. The interior packaging is defined as anything which the outer package must be opened to access, e.g. IFU, product manual, safety information, brochures.

Alternatively, there may be unique QR codes printed on the outer and inner packaging of a product, i.e., 804 and 808 are different. In this case, the two QR codes, although linked to the same product, may serve different purposes. For example, the QR code 808 on the interior material might only be meant to be scanned by the consumer, being inaccessible without opening the package. It could be easily used in the anti-counterfeiting measures described above. Meanwhile, the QR code 804 on the outer packaging is less useful for that particular implementation of anti-counterfeiting measures, since it can be easily scanned without opening the package, perhaps by consumers wishing to find out more about the product before they buy it. However, because it is easily accessible, it can be used by other participants on the supply chain without opening the product packaging to log items as having passed through certain check points or pass other information up or down the supply chain.

Figure 9:
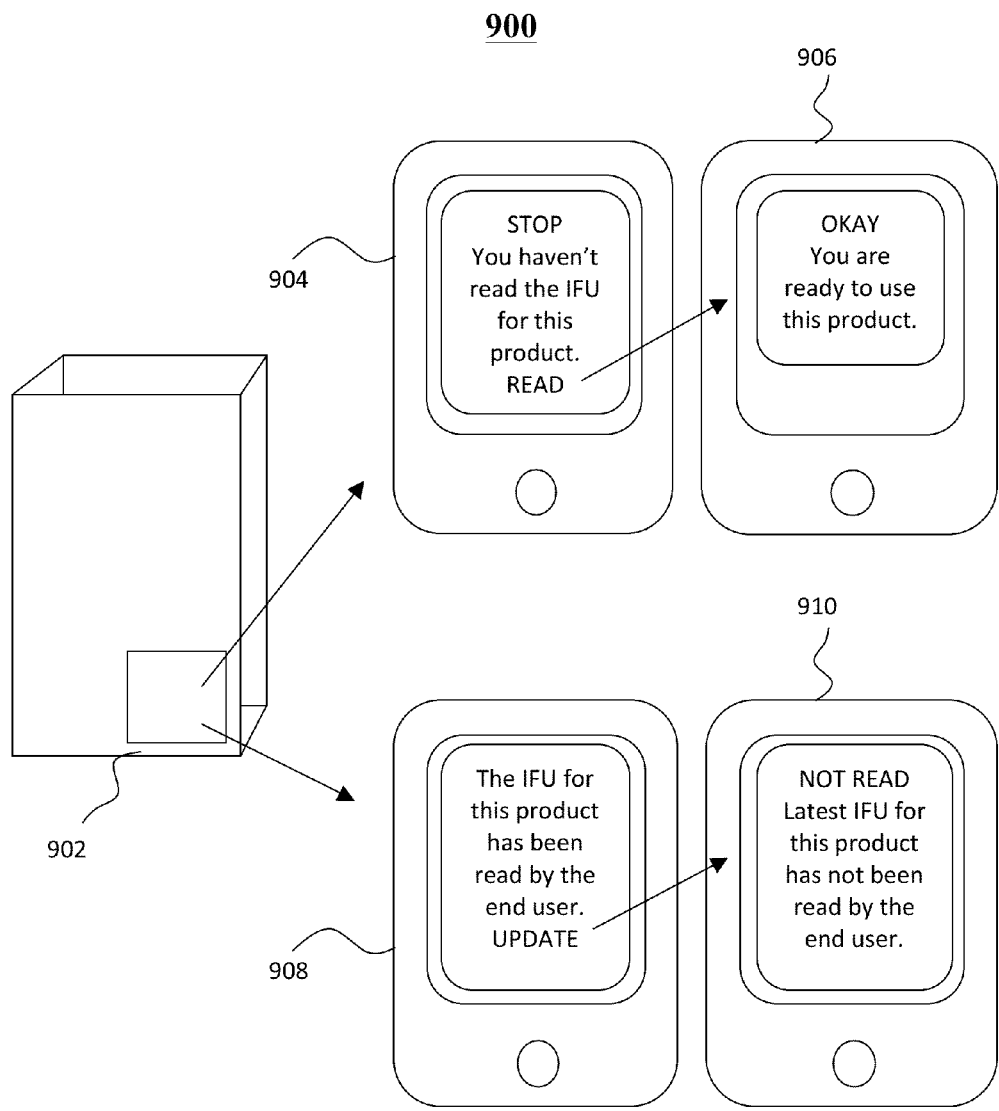
FIG. 9 is an illustration of an item-level QR code being used to direct users of medical equipment to read the IFU for said equipment or to alert said users to updates to the IFU, and allowing manufacturers to easily post an alert about updates to a product IFU.

FIG. 9 shows a potential implementation of the invention which would allow consumers easy access to electronic instructions for use (eIFUs) for products such as surgical equipment. Scanning the QR code 902 in that case would display dynamic content indicating that the consumer either has (906) or has not (904) read the latest version of the IFU, as well as providing a link or download of the IFU. If the consumer has viewed the IFU through that link/download, the dynamic content will indicate that they have read the latest version of the IFU. However, if the consumer has never accessed this page before, or if a new version of the IFU (the most recent electronic version of the IFU) has been published since the last time the consumer viewed the IFU, the dynamic content will indicate that the consumer should read the current IFU before using the product.

This implementation could also provide an interface for the manufacturer, or other entities along the supply chain, to monitor whether consumers of the product had read the IFU and to publish updated versions of the IFU for a product (908). When an update is published, consumers and other entities involved in the supply chain would once again see that the current version of the IFU had not been read by the consumer (904, 910).

Figure 10:
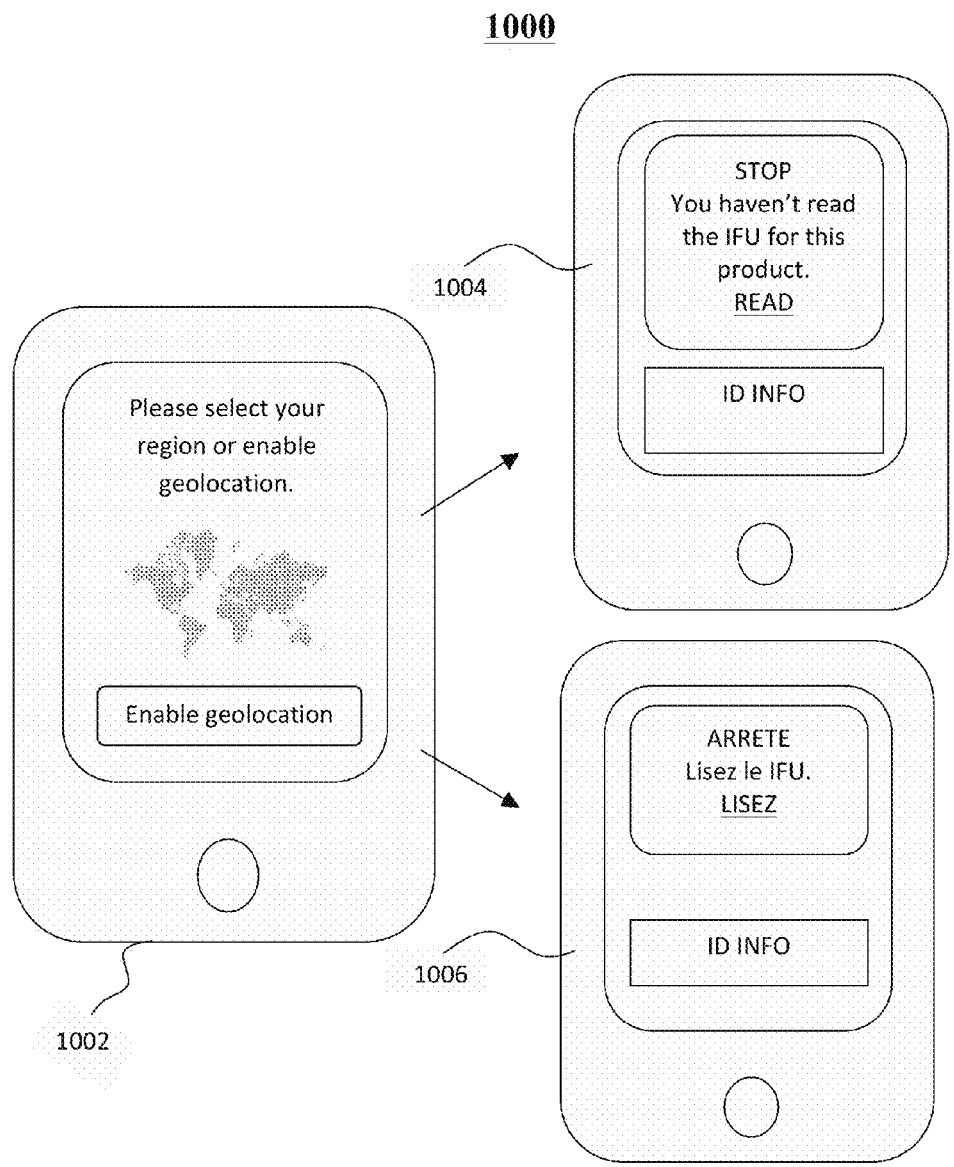
FIG. 10 illustrates a potential application of mobile phones' geolocation functions to distribute content to users in a language appropriate to their location.
Figure 11:
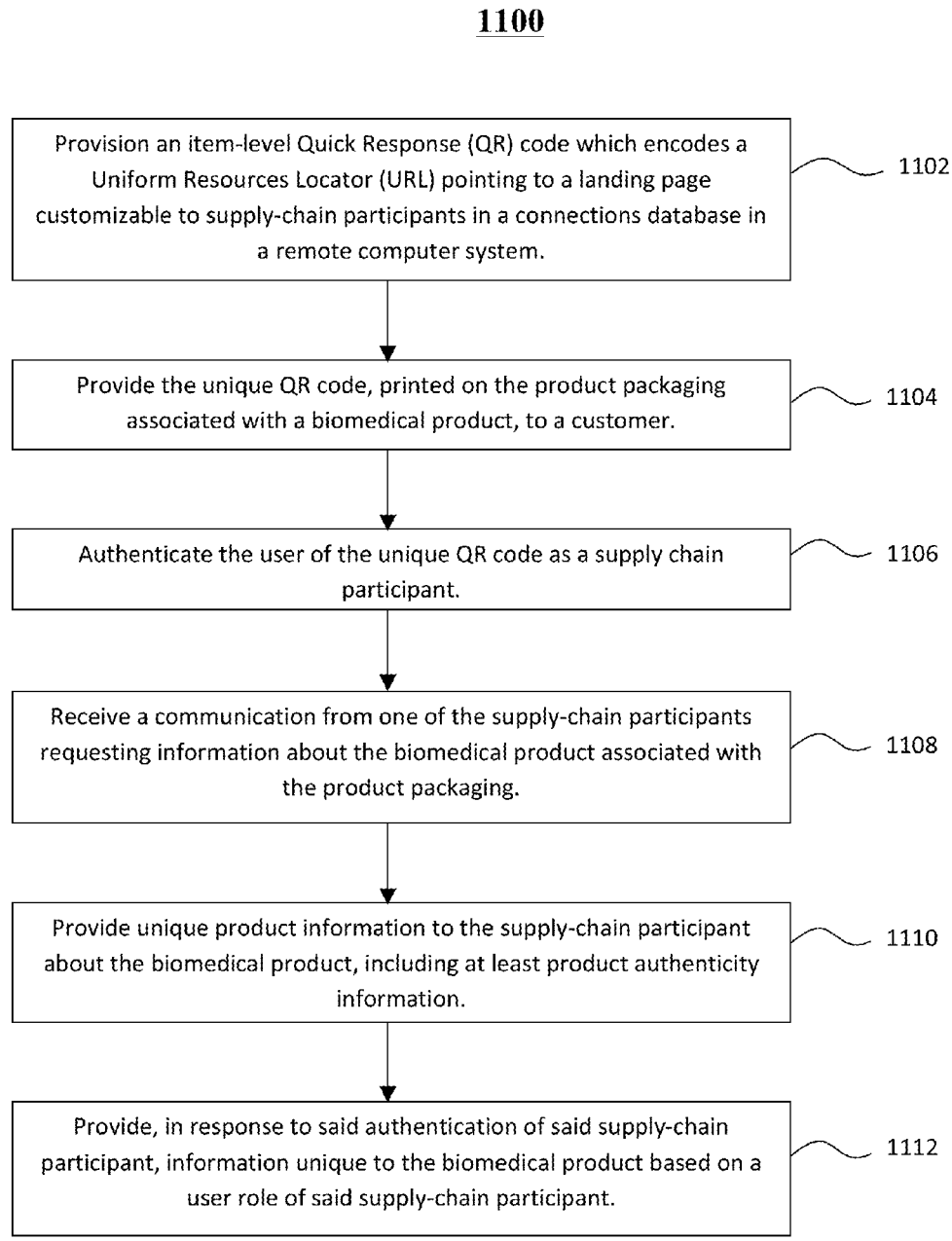
FIG. 11 is a flowchart of a method for tracking and tracing a biomedical product to ensure product authenticity, in accordance with one embodiment of the invention.

FIG. 10 illustrates another embodiment of this invention which could make IFUs or other supplementary material more accessible to the consumer by using geolocation to determine the appropriate language to present said material in. In this embodiment, upon either scanning the QR code, following a link, or requesting to download the material, the consumer would be prompted to either choose their region from a map, drop down, etc. or enable geolocation (1002). Based on the physical position of the device which performs the scan, the material would be presented either exclusively or initially in an appropriate language to the consumer (1004, 1006).

One embodiment of the present invention is a collaborative method for tracking and tracing a biomedical product. The method involves concerted usage of a printer component such as an industrial label printing machine, an electronic network communication channel such as broadband or wireless Internet, one or more application servers, and one or more database servers. A server comprises at least a computer processor, memory, secondary storage, and network connectivity hardware that is capable of transmitting and receiving electronic signals on the electronic network communication channel. This method is carried out by multiple supply chain participants, each assuming a user role that governs their interactive actions upon biomedical product data.

The printer component is used to print regulation required data onto individual biomedical product packages. It should be noted also that this product packaging can fully enclose the biomedical product item, so the printing need not be on the item itself. This is generally done by the manufacturer user role within the supply chain. For a biomedical product, this involves sending over the network to a printer an electronic command to print along with the data to print. The data could be an image of a drug label or an image of a medical device label in the regulatory required format. For a medical device, this would be a device label that comprises the trademarked name of the device, a reference number, lot number, a use-by date, indication of whether it is single use, temperature limits, "do not use if package is damaged" warnings or other warnings, quantity indicator, manufacturer business name, address, phone number, web URL, scannable bar code, sketch of the device, and industry-standard symbols representing various properties of the device.

The printer component is also used to print a scannable Quick Response (QR) code on each product item's packaging. The QR code can represent raw alphanumeric data or it could represent a URL. When the QR code represents a URL, it has the advantage of not being limited in the amount of data it can hold, since the URL is simply a link and effectively shifts responsibility of data dissemination to the server that responds to the URL request when invoked. The response to an invocation of the URL is a landing page on which there is regulation required data, which can repeat the data that is physically printed on the product item label and may include more specific data not found on the product item label. Most importantly, this landing page can include the most recent version of data, such as the most recent version of an electronic instructions for use (IFU) document, which is important for data that changes over time.

The printer could print the same QR code on the packaging of all product items, however, it is most effective if the printer prints a unique QR code on each package. This is done by using a code generator to create per-item codes and configuring a web server to respond to URL's that include this code. An example URL would be http://test.com/49gu0324, whereby 49gu0324 is the code. The codes may be randomly or purposely generated and are stored in a database, with subsequently generated codes checked against the database for collisions. This way, when the URL above is invoked, a lookup is done for the code 49gu0324 and data associated with that code is returned as a structured response. The structured response could be a landing page represented in HTML, or it could be a JSON data object, an XML document, or even an encrypted string. The structured response could even include other URL's made available to further invoke. Instead of or in addition to printing unique QR codes representing unique URL's, the printer could print the unique URL itself on the package.

Supply chain participants interact with the product items bearing this printed code by scanning the printed code with a smartphone, transcribing the URL, or using other code-reading machinery. Before doing so, a supply chain participant could identify herself by authenticating, or can simply scan anonymously. Each supply chain participant invokes the URL generally to read the data associated with the individual product item, but also has the option to write data. An example of this is if the supply chain participant is a patient and is writing how he feels after taking the drug item—he may write "I feel wonderful" which may be done by utilizing a text box within the landing page returned by the first invocation of the URL. Hitting a "Send" button may invoke another or the same URL that sends the data via a POST request along with POST data. A script on the server would process the POST request for the "I feel wonderful" data, which is then written to the database and associated with the particular drug item. When a supply chain participant writes data using the URL, he may also include a directive such as "warning", "comment", "feedback", "immediate help requested", or others. A directive is a meta-data component that accompanies the supply chain participant data that helps other supply chain participants further understand what the data means or what they should do with it. The system that transacts the product item data may interpret the directive in various ways. For example, a "warning" directive that comes from a manufacturer posting information about side effects recently discovered regarding an outstanding drug item may cause the system to display large red warning text on drug item landing pages, such as "WARNING: Do not take this drug if you are pregnant." The same supply chain participant data without the accompanying "warning" directive may just simply display "Do not take this drug if you are pregnant" on the landing page in plain vanilla format (i.e. without any alterations to font color, font size, position on the page, etc.).

The nature of having each individually unique URL for each product item serve as a read/write mechanism, especially for data writes to be made from any supply chain participant having identified themselves by role, is an important feature.

The method makes use of rules that govern the structure and content of landing pages. These rules are implemented as data objects that contain a predicate and consequence (the parts of a conditional IF . . . THEN statement). A rules engine such as JBoss Drools is used to manage a set of rules and run a process that fires the rules based on an event feed. Additionally, rules are categorized and placed into appropriate rule sets. The rules can be architected to be order independent or follow a priority-ordered execution stack. Dynamic rules are created as data is submitted to the system through the URL by supply chain participants. Static rules are created before the system is even up and running—they would be inherent rules within the system. Initializing a rule involves loading the rule into a running rules engine subroutine's memory. Static rules may be created before the host system is in operation and initialized when the rule engine is first started, while dynamic rules may be both created and initialized while the rules engine is running.

One type of rule is a regulation rule that reacts to regulation required data. The nature of having each individually unique landing page for each product item react to the current state of the regulatory data dissemination requirements of a governing body that apply to the product item, is a much-needed feature. Currently, industry does not get along well with any change in the state of regulation due to the traditionally large cost of infrastructure change to comply with the regulation change, which is why there is inertia in the state of track and trace guidelines from the FDA. This step is the key to solving the industry inertia because it is what enables the invention to be agile toward changing regulation by encoding the regulation required data in easily updatable rule set. For example, if the FDA tomorrow came up with a format guideline for a drug package's e-Pedigree to be encoded as a JSON response, a rule set would be created in the rules system that would look something like this: "Rule: when client requests e-Pedigree data ep, intercept the original request and return to_json(ep)." The regulation rule can govern either the structure, content, or even presentation of regulation required data on the landing page. Presentation can be expressed as something like "Rule: when client requests landing page, return to_html5_table(sni, batch_no, exp_date, fda_warnings[ ], ifu)." In addition to these dynamic regulation data rules, there can be more static regulation rules such as those predetermined for certain locales. For example, some drug sales are illegal in certain countries, so there might be a rule like "Rule: when client requests landing page and geolocation(client).within(restricted states[ ]), return "STOP—you must dispose of this item because it is illegal for you to possess it in your current locale."

Another type of rule is a supply chain participant rule that reacts to supply chain participant data and a directive. The nature of having each individually unique landing page for each product item react to supply chain participant data and a directive provided by a supply chain participant that applies to the product item, is a much-needed feature. A supply chain participant could be a manufacturer, wholesaler, distributor, pharmacy, consumer, etc. The system would be set up so that each supply chain participant can add data to the individual drug package's collection of data when needed, along with a directive which is essentially an actionable meta-data about the supply chain participant data. A major example of this is when a recall must be made on a particular batch 003 of drug X. The supply chain participant data in this case would be a codification of "Recall has been made for drug X, batch 003" and the directive would be "show directions for return." The first rule that picks up on this data would look like "Rule: when client requests landing page lp for drug X and there exists supply chain participant data for drug X that contains 'recall', return batch=='003' ? prepend(lp, recall_notice(X)): lp". Another rule would cover the directive to "show directions for return" which would look like "Rule: when a call to recall_notice( ) is made, intercept the call and return directive==SHOW_DIRECTIONS_FOR_RETURN ? recall notice with return directions(X): recall_notice(X)."

Another type of rule is a user role rule that reacts to a user role identified with a current user. The current user is the person or thing that is interacting with a landing page, and the user role is identified either by direct identification or by inference. Direct identification can be achieved through an authentication system such as a log in involving a username, password, e-mail, or other unique user verification data. Inference can be achieved by using the context of a landing page client such as geo-location or even just a volunteered user role type indicator if the client is presented with buttons that say "I am a surgeon" or "I am a patient" and clicks one of them. A user role rule is more likely to be implemented as a static rule rather than a dynamic rule, since the permissions for user roles of supply chain participants are generally static and since there would be fewer data addition events concerning user roles. Such user role blockage situations, like when a patient posts data and does not want any supply chain participant to see it except the prescribing doctor, can be implemented either as a user role rule or a supply chain participant rule. An example of a static user role rule for a drug package would be "Rule: when client requests landing page lp and user_role(client)!=DOCTOR, return enforce_hipaa_data_block(lp)" since in this case it is assumed that there will always be an HIPAA data enforcement needed when the user role of the viewing user is anything but a doctor. It may even be more specific and make a further check to see if the doctor is authorized to view the particular patient-submitted supply chain participant data regarding the drug package in question. The nature of having each individually unique landing page for each product item react to the user role identified for a scanning supply chain participant being an innovative way to categorize and limit certain supply chain participants from making certain actions with both the data and other supply chain participants, is an important feature for the heavily regulated biomedical industry.

The invocation of a landing page is made by any client (presumably one of the supply chain participants) through the unique URL—the client in this case would be a "scanning supply chain participant" because to access the unique URL they would most likely have scanned the QR code on the product item package using a smartphone or other camera-enabled device. A computer system receives, via the unique URL, a scan of the unique QR code by a scanning supply chain participant and then identifies the scanning supply chain participant with a user role. If there is no way to infer or identify the scanning supply chain participant's user role, there is a default of him being the consumer or patient. This is because the consumer is presumed to be the least likely to have an account on the system before he starts using it, whereas industrial supply chain participants like the manufacturer, wholesaler, or distributor, are much more likely to have an account on the system and be disciplined to be using their account as part of standard business practice.

Finally, the regulation rule, supply chain participant rule, and user role rule are all combined to affect the response of the URL invocation. In the majority of cases, it would affect the structure, content, and presentation of a web landing page response. In some cases, it may affect encoded responses such as JSON or XML representations of the same data that would have been viewed on a landing page—this would happen in the situation where the URL was being used in an API mode. Multiple supply chain participants submit data to the same URL, each data of which affects the response of the subsequent URL invocation. These data are combined to produce a resultant response by means of the before-mentioned rules. The nature of the collaboration of multiple supply chain participants in contributing data via the unique URL for each individual product item leads to a socially-constructed unique landing page as a result, which represents a level of productive communication unheard of in the industry currently. Furthermore, the communication is done at the granularity level of an item-level package, which allows for much more interesting one-to-one data collection. The final useful result is an item-level unique landing page whose structure and content has been "crowdsourced" whereby the crowd is made up of supply chain participants that are part of the pedigree of product handling for the biomedical product item associated with the unique URL.

In one particular embodiment of applying the combined rules on a particular drug package—in this case a pill bottle with a unique QR printed on its label and also bearing printed regulation required data, the consumer/patient enters supply chain participant data that is personal only to him. For example, he creates and submits an active calendar to help himself adhere to a schedule for prescription medication involving the drug package. Then, using a segment of the landing page interface that allows him to create rules on his data, he sets a user role rule to block the data from being viewed by any other supply chain participant other than him. Then he sets a supply chain participant rule that makes the landing page show him his calendar as the first-displayed widget on the landing page for the particular drug package he owns, with a directive that shows "WARNING—you have missed X days of this medication" if there has been 3 consecutive days in which he has not marked "taken" on his active calendar. The system applies a regulation rule that shows him the specific details of the drug he has below the active calendar on the landing page. He then makes use of this landing page configuration to make sure he is taking medication on the schedule he is supposed to adhere to, according to his primary care physician, making it a habit to scan the unique QR code on the pill bottle every day. Finally, when he runs out of pills and needs to refill the prescription, he may use the same bottle to refill at the pharmacy or even get a new bottle with a new QR code and landing page, which he initializes by populating it with active calendar data from the old pill bottle. In another embodiment of this scenario, the patient can opt to share his active calendar data with another supply chain participant, perhaps having been incentivized to do so by a manufacturer since this data is highly valuable for a manufacturer and other parties to predict drug sales, observe real-time drug usage, among other benefits.

One embodiment of the present invention is a collaborative method for tracking and tracing a biomedical product that also includes using the printer to print an Instructions for Use (IFU) document that is stored with the biomedical product item and contains a unique item-level QR code that leads to a unique web landing page. That unique web landing page can be configured to always redirect to the most recent version of the IFU document. In the case of a surgeon using the IFU on a medical device, using a simple scan the surgeon would always be directed to the most updated version of the IFU, which may contain updates from the manufacturer about best usage patterns, safety concerns, warnings, or other relevant information for the surgeon's task at hand. Finally, this electronic IFU (e-IFU) document can be associated with a Unique Device Identifier (UDI) as mandated by the FDA, also serving as a way to track the usage and safety of a medical device at the item level. An example of how this might be used for safety purposes is tracking whether and when the e-IFU has been accessed, to ensure that the surgeon or his staff has read the necessary information. To implement, the unique landing page provides an indicator of whether the most recent electronic version of the IFU document has been previously accessed via said unique landing page. Even if an IFU document has already been read and marked as read, the indicator will be reset when the manufacturer posts a new version of the IFU document. The landing page can also provide a date and time stamp of when the most recent electronic version of the IFU document was previously accessed via the unique landing page, as well as record new date and time stamps for future scans.

Another embodiment of the present invention involves a local regulation which causes the unique landing page to be reconfigured to comply with such local regulation. First, a supply chain participant writes supply chain participant data to the unique URL that serves as an indicator of the local regulation. An indicator of the local regulation is any information that infers the jurisdiction or locale from which the system can look up what rules apply. An example is if the supply chain participant writes his geo-location, which indicates that he is in Angola and that the local rules of the country of Angola apply to the unique landing page he accesses with his mobile device. If, for example, it is illegal to sell, use, or even possess the drug package in the supply chain participant's possession in Angola, that fact will be encoded as a local regulation which then causes the unique landing page response to be modified to show "WARNING—it is illegal to sell, use, or possess this product in Angola. Dispose of this product immediately" along with various disclaimers of liability. In this case, when the supply chain participant data is a geo-location, it is offered by the supply chain participant because of generally accepted and implemented privacy rules on mobile browsers that require an opt-in to share geo-location in order to comply those privacy rules.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

While the present invention has been particularly shown and described with reference to embodiments thereof, it will be understood by those skilled in the art that various other changes in the form and details may be made without departing from the scope of the present invention as defined by the claims.

What is claimed is:

1. A method for tracking and tracing a product through a supply-chain utilizing data received from authorized supply-chain participants, comprising the steps of:

printing on a product packaging a unique Quick Response (QR) code which encodes a unique Uniform Resource Locator (URL) having a one-to-one mapping with an individual item of said product;

providing a unique landing page showing at least data about said individual item contained in said product packaging in response to a scan of said unique QR code to a scanning supply chain participant;

receiving via the unique landing page said unique QR code printed on said product packaging containing said individual item of said product from the scanning supply chain participant;

receiving product usability data comprising at least information about usability of said individual item from an authorized supply chain participant;

generating item-specific usability data and a directive related to use, using a computer processor, based on the product usability data received from the authorized supply chain participant and the unique QR code; and presenting said unique landing page comprising said item-specific usability data to said scanning supply chain participant.

2. The method of claim 1, wherein the scanning supply chain participant is an end-user consumer.

3. The method of claim 1, wherein the scanning supply chain participant is a pharmacy.

4. The method of claim 1, wherein the scanning supply chain participant is a distribution center.

5. The method of claim 1, wherein the authorized supply chain participant is a manufacturer.

6. The method of claim 1, wherein the authorized supply chain participant is a pharmacy.

7. The method of claim 1, further comprising:

printing on the product packaging regulation required data comprising product safety information about said individual item of the product contained within said product packaging from a manufacturer of said product.

8. The method of claim 7, further comprising:

applying, utilizing the computer processor, a regulation rule based on the regulation required data that governs in part how said unique landing page is presented, to modify said unique landing page presented to said scanning supply chain participant, wherein said regulation required data comprises data that is required by one or more regulatory guidelines from a regulatory agency that regulates the product.

9. The method of claim 1, further comprising:

providing a printed Instructions for Use (IFU) document stored with said individual item of said product, said IFU document comprising printed instructions and the unique QR code; and providing a most recent electronic version of said IFU document, wherein said unique landing page comprises a link to said most recent electronic version of said IFU document.

10. The method of claim 9, further comprising:

providing an indicator of whether said most recent electronic version of said IFU document has been previously accessed via said unique landing page; and providing a date and time stamp of when said most recent electronic version of said IFU document was previously accessed via said unique landing page.

11. A system for tracking and tracing a product utilizing data received from authorized supply-chain participants, comprising:

at least one processor for executing stored program code;

at least one non-transitory program memory for storing program code, operatively connected to the processor, which when executed causes the processor to execute a process comprising the steps of:

printing on a product packaging a unique Quick Response (QR) code which encodes a unique Uniform Resource Locator (URL) having a one-to-one mapping with an individual item of said product;

providing a unique landing page showing at least data about said individual item contained in said product packaging in response to a scan of said unique QR code to a scanning supply chain participant;

receiving via the unique landing page said unique QR code printed on said product packaging containing said individual item of said product from the scanning supply chain participant;

receiving product usability data comprising at least information about usability of said individual item from an authorized supply chain participant;

generating item-specific usability data and a directive related to use based on the product usability data received from the authorized supply chain participant and the unique QR code; and presenting said unique landing page comprising said item-specific usability data to said scanning supply chain participant.

12. The system of claim 11, wherein the scanning supply chain participant is an end-user consumer.

13. The system of claim 11, wherein the scanning supply chain participant is a pharmacy.

14. The system of claim 11, wherein the scanning supply chain participant is a distribution center.

15. The system of claim 11, wherein the authorized supply chain participant is a manufacturer.

16. The system of claim 11, wherein the authorized supply chain participant is a pharmacy.

17. The system of claim 11, wherein the stored program code comprises additional program code, which when executed further causes the system to perform the step of:

printing on the product packaging regulation required data comprising product safety information about said individual item of the product contained within said product packaging from a manufacturer of said product.

18. The system of claim 17, wherein the stored program code comprises additional program code, which when executed further causes the system to perform the step of:

applying a regulation rule based on the regulation required data that governs in part how said unique landing page is presented, to modify said unique landing page presented to said scanning supply chain participant, wherein said regulation required data comprises data that is required by one or more regulatory guidelines from a regulatory agency that regulates the product.

19. The system of claim 11, wherein the stored program code comprises additional program code, which when executed further causes the system to perform the steps of:

providing a printed Instructions for Use (IFU) document stored with said individual item of said product, said IFU document comprising printed instructions and the unique QR code; and providing a most recent electronic version of said IFU document, wherein said unique landing page comprises a link to said most recent electronic version of said IFU document.

20. The system of claim 19, wherein the stored program code comprises additional program code, which when executed further causes the system to perform the steps of:

providing an indicator of whether said most recent electronic version of said IFU document has been previously accessed via said unique landing page; and providing a date and time stamp of when said most recent electronic version of said IFU document was previously accessed via said unique landing page.

* * * * *